US007645903B2

(12) United States Patent
Axén et al.

(10) Patent No.: US 7,645,903 B2
(45) Date of Patent: Jan. 12, 2010

(54) USE OF UREA VARIANTS AS AFFINITY LIGANDS

(75) Inventors: Andreas Axén, Uppsala (SE); Herbert Baumann, Uppsala (SE); Enrique Carredano, Uppsala (SE); Anna Grönberg, Uppsala (SE); Elles Steensma, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 555 days.

(21) Appl. No.: 10/531,783

(22) PCT Filed: Sep. 12, 2003

(86) PCT No.: PCT/SE03/01434

§ 371 (c)(1),
(2), (4) Date: Apr. 18, 2005

(87) PCT Pub. No.: WO2004/039765

PCT Pub. Date: May 13, 2004

(65) Prior Publication Data

US 2006/0014735 A1    Jan. 19, 2006

(30) Foreign Application Priority Data

Oct. 31, 2002  (SE) ................................. 0203226
Dec. 20, 2002  (SE) ................................. 0203878

(51) Int. Cl.
  *C07C 275/00*   (2006.01)
  *C07D 213/81*   (2006.01)
  *A61P 37/00*    (2006.01)
  *C07D 233/34*   (2006.01)
  *A61K 31/17*    (2006.01)

(52) U.S. Cl. .......................... 564/48; 564/52; 564/53; 564/54

(58) Field of Classification Search ................. None
  See application file for complete search history.

(56) References Cited

U.S. PATENT DOCUMENTS 4,977,247 A     12/1990  Fahnestock et al.
  5,356,904 A *  10/1994  Freidinger et al. .......... 514/312
  2002/0193633 A1 12/2002  Feng et al.

FOREIGN PATENT DOCUMENTS

| EP | 0327365 | 2/1989 |
| EP | 0743067 | 5/1996 |
| WO | WO 97/27752 | 8/1997 |
| WO | WO 02/076930 | 10/2002 |
| WO | WO 02/083628 | 10/2002 |

OTHER PUBLICATIONS

STN structure search results printout for US 5,356,904. Granted on Oct. 18, 1994.*
Akii, et al., "Prevention of crop plant damage cased by N-substituted phenylcarbamoylamino acid herbicides", *STN International*, CAPLUS accession No. 1978:165488.
Bazin, H., et al., "Rat Monoclonal Antibodies. II. A Rapid and Efficient Method of Purification from Ascitic Fluid or Serum", *Journal of Immunological Methods*, vol. 71, 1984, p. 9-16.
Bonwick, G., et al., "Production of murine monoclonal antibodies against sulcofuron and flucofuron by in vitro immunization", *Journal of Immunological Methods*, vol. 196, 1996, p. 163-173.
Chacko, S., et al., "Structural Studies of Human Autoantibodies", *The Journal of Biological Chemistry*, vol. 271, No. 21, 1996, pp. 12191-12198.
Hoshii, Y., "Useful polyclonal antibodies against synthetic peptides corresponding to immunoglobulin light chain constant region for immunohistochemical detection of immunoglobulin light chain amyloidosis", *Pathology International*, vol. 51, 2001, p. 264-270.
Krämer, P., et al., "Flow injection immunoaffinity analysis (FIIAA)—A screening technology for atrazine and diuron in water samples", *Analytica Chimica Acta*, vol. 399, 1999, p. 89-97.
Lawrence, J., "Use of immunoaffinity chromatography as a simplified cleanup technique for the liquid chromatographic determination of phenylurea herbicides in plant material", *Journal of Chromatography*, vol. 732, 1996, p. 277-281.
McElroy, N., et al., "QSAR and Classification of Murine and Human Soluble Epoxide Hydrolase Inhibition by Urea-Like Compounds", *Journal of Medicinal Chemistry*, vol. 46, 2003, p. 1066-1080.
Schneider, P., "A Highly Sensitive and Rapid Elisa for the Arylurea Herbicides Diuron, Monuron, and Linuron", *J. Agric. Food Chem.*, vol. 42, 1994, p. 413-422.
Schoenzetter, E., "Rapid Sample Handling in Microcolumn-Liquid Chromatography Using Selective In-line Immunoaffinity Extraction", *J. Microcolumn Separations*, vol. 12, 2000, p. 316-322.

* cited by examiner

*Primary Examiner*—Daniel M Sullivan
*Assistant Examiner*—Yevegeny Valenrod
(74) *Attorney, Agent, or Firm*—Yonggang Ji

(57) ABSTRACT

The present invention relates to an IgG-binding compound, which more specifically has affinity for human IgGs of κ-type and functional derivatives thereof. More specifically, the compound according to the invention comprises an N,N-alkylated urea moiety located between an aromatic part and another part, which is a linear or cyclic substituted or unsubstituted aliphatic group. The compound binds to a pocket-shaped binding site present on all human IgG κ-Fabs, which site is located between the two domains (CH1 and CL) of its constant part. Accordingly, the compound according to the invention is a ligand for human IgGs of κ-type, and consequently, the invention also relates to a separation matrix for affinity chromatography, which matrix comprises said compound, as well as to other uses of the compound.

10 Claims, 12 Drawing Sheets

Figure 1: Synthetic route to variations

R1 = Cl, F, OMe
R2 = Cl, F
R3 = H, Me
R4 = H, Me
R5 = H, Me

Figure 3: Illustrative compounds
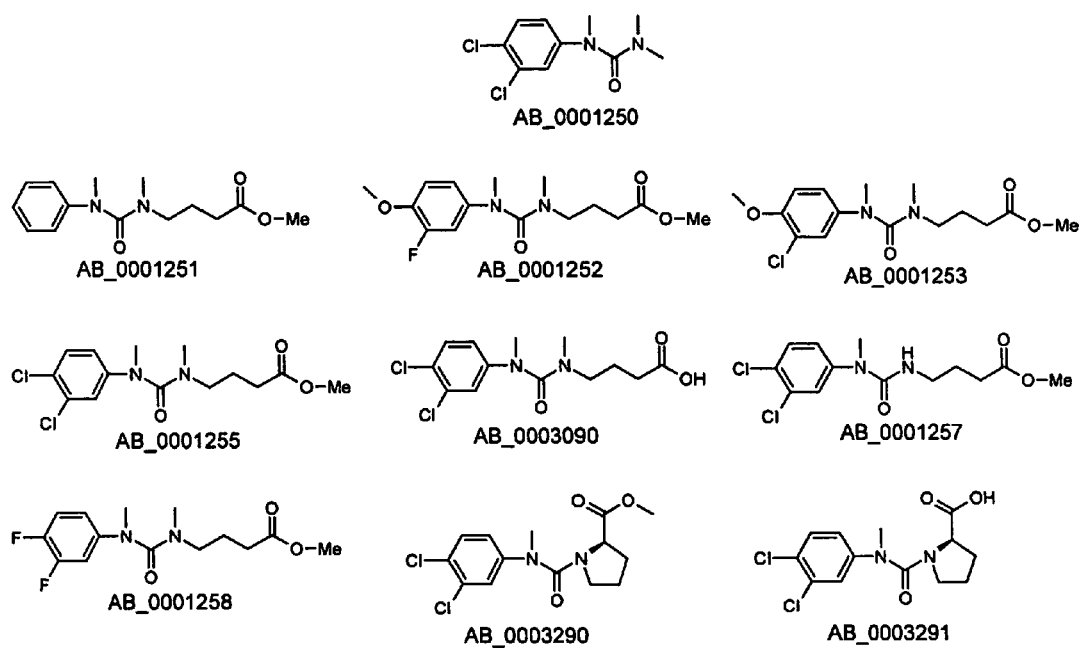

Figure 4: Orthographic views
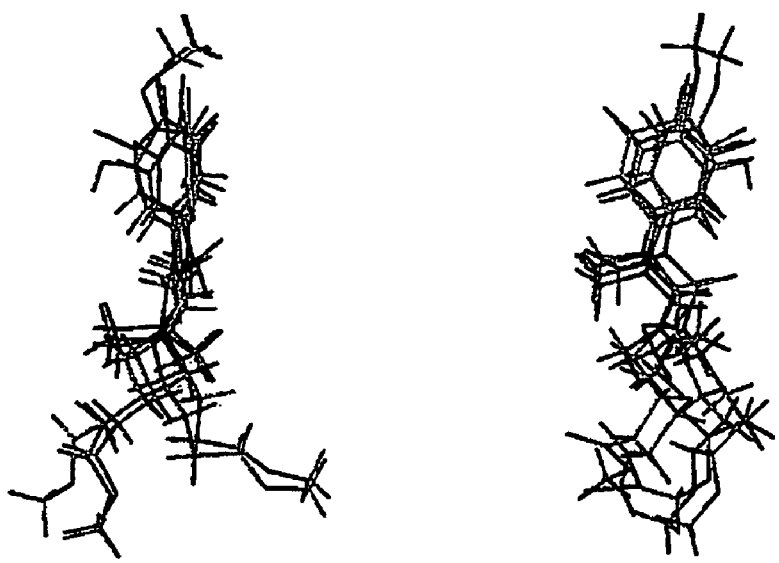

Figure 5A-E: Orthographic views of the docked compounds AB_000125[1-5].
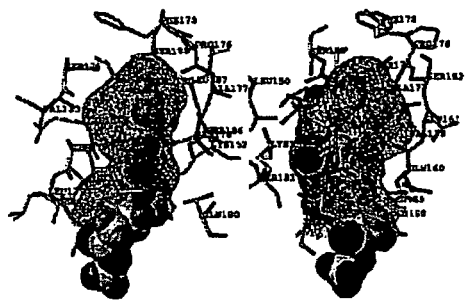
Fig 5A: AB_0001251
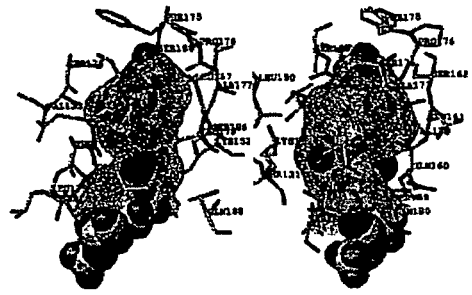
Fig 5B: AB_0001252
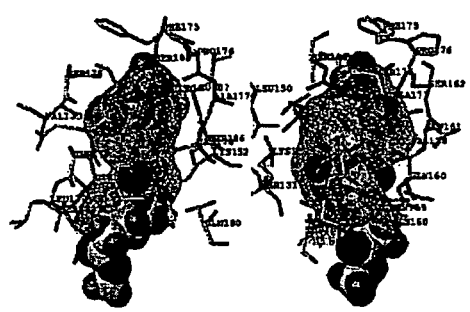
Fig 5C: AB_0001253
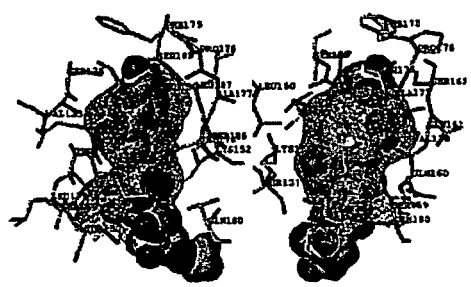
Fig 5D: AB_0001254
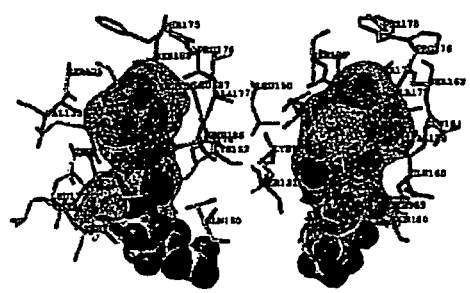
Fig 5E: AB_0001255

Fig 6a kappa light chain

```
ATOM    928  N    GLN L 124     -44.718  27.024  79.393  1.00 37.64           N
ATOM    929  CA   GLN L 124     -43.847  25.897  79.535  1.00 38.32           C
ATOM    930  C    GLN L 124     -44.309  25.088  80.734  1.00 39.17           C
ATOM    931  O    GLN L 124     -44.458  23.876  80.578  1.00 40.06           O
ATOM    932  CB   GLN L 124     -42.414  26.311  79.745  1.00 37.76           C
ATOM    933  CG   GLN L 124     -41.615  25.026  79.581  1.00 34.56           C
ATOM    934  CD   GLN L 124     -40.133  25.152  79.698  1.00 34.95           C
ATOM    935  OE1  GLN L 124     -39.440  24.138  79.682  1.00 34.80           O
ATOM    936  NE2  GLN L 124     -39.569  26.344  79.820  1.00 39.75           N
ATOM    954  N    SER L 127     -46.898  22.499  80.067  1.00 50.58           N
ATOM    955  CA   SER L 127     -46.559  21.169  79.588  1.00 49.80           C
ATOM    956  C    SER L 127     -45.890  20.274  80.637  1.00 49.81           C
ATOM    957  O    SER L 127     -45.283  19.248  80.318  1.00 50.44           O
ATOM    958  CB   SER L 127     -45.674  21.333  78.368  1.00 50.26           C
ATOM    959  OG   SER L 127     -44.618  22.263  78.551  1.00 51.43           O
ATOM    960  N    GLY L 128     -45.954  20.623  81.919  1.00 48.65           N
ATOM    961  CA   GLY L 128     -45.371  19.786  82.925  1.00 47.11           C
ATOM    962  C    GLY L 128     -43.851  19.873  82.985  1.00 46.88           C
ATOM    963  O    GLY L 128     -43.322  19.013  83.700  1.00 46.88           O
ATOM    964  N    THR L 129     -43.091  20.805  82.358  1.00 46.66           N
ATOM    965  CA   THR L 129     -41.625  20.919  82.516  1.00 43.85           C
ATOM    966  C    THR L 129     -41.246  22.341  82.832  1.00 37.58           C
ATOM    967  O    THR L 129     -42.031  23.269  82.637  1.00 35.77           O
ATOM    968  CB   THR L 129     -40.785  20.528  81.250  1.00 48.03           C
ATOM    969  OG1  THR L 129     -41.566  20.726  80.058  1.00 54.58           O
ATOM    970  CG2  THR L 129     -40.269  19.111  81.408  1.00 49.23           C
ATOM    976  N    SER L 131     -37.741  24.856  82.399  1.00 29.71           N
ATOM    977  CA   SER L 131     -36.337  25.100  82.108  1.00 27.40           C
ATOM    978  C    SER L 131     -35.958  26.455  82.672  1.00 24.38           C
ATOM    979  O    SER L 131     -36.663  27.454  82.446  1.00 23.59           O
ATOM    980  CB   SER L 131     -36.097  25.078  80.593  1.00 29.26           C
ATOM    981  OG   SER L 131     -36.672  23.985  79.880  1.00 28.43           O
ATOM    989  N    VAL L 133     -32.859  29.248  82.770  1.00 23.53           N
ATOM    990  CA   VAL L 133     -31.671  29.552  81.985  1.00 21.58           C
ATOM    991  C    VAL L 133     -30.829  30.592  82.700  1.00 21.93           C
ATOM    992  O    VAL L 133     -31.363  31.514  83.297  1.00 22.42           O
ATOM    993  CB   VAL L 133     -32.042  30.112  80.607  1.00 21.06           C
ATOM    994  CG1  VAL L 133     -30.831  30.026  79.693  1.00 25.56           C
ATOM    995  CG2  VAL L 133     -33.149  29.296  79.958  1.00 24.10           C
ATOM   1188  N    GLY L 157     -26.853  18.788  90.054  1.00 53.00           N
ATOM   1189  CA   GLY L 157     -26.116  18.154  88.943  1.00 52.14           C
ATOM   1190  C    GLY L 157     -27.023  17.720  87.749  1.00 51.94           C
ATOM   1191  O    GLY L 157     -26.809  16.631  87.208  1.00 52.06           O
ATOM   1192  N    ASN L 158     -28.025  18.503  87.273  1.00 50.46           N
ATOM   1193  CA   ASN L 158     -28.946  18.183  86.142  1.00 46.46           C
ATOM   1194  C    ASN L 158     -29.116  19.347  85.106  1.00 44.90           C
ATOM   1195  O    ASN L 158     -30.222  19.704  84.625  1.00 40.45           O
ATOM   1196  CB   ASN L 158     -30.312  17.839  86.692  1.00 47.64           C
ATOM   1197  CG   ASN L 158     -30.916  19.055  87.386  1.00 52.21           C
ATOM   1198  OD1  ASN L 158     -30.438  19.529  88.430  1.00 47.79           O
ATOM   1199  ND2  ASN L 158     -31.930  19.646  86.768  1.00 55.19           N
ATOM   1200  N    SER L 159     -27.980  19.972  84.739  1.00 41.19           N
ATOM   1201  CA   SER L 159     -27.943  21.083  83.811  1.00 38.82           C
ATOM   1202  C    SER L 159     -27.136  20.769  82.554  1.00 38.54           C
ATOM   1203  O    SER L 159     -26.262  19.891  82.610  1.00 39.32           O
ATOM   1204  CB   SER L 159     -27.323  22.257  84.505  1.00 32.87           C
ATOM   1205  OG   SER L 159     -26.007  21.915  84.912  1.00 34.12           O
ATOM   1206  N    GLN L 160     -27.397  21.485  81.451  1.00 37.38           N
ATOM   1207  CA   GLN L 160     -26.575  21.389  80.266  1.00 35.88           C
ATOM   1208  C    GLN L 160     -26.118  22.789  79.886  1.00 32.74           C
ATOM   1209  O    GLN L 160     -26.831  23.765  80.112  1.00 28.45           O
ATOM   1210  CB   GLN L 160     -27.325  20.798  79.077  1.00 40.64           C
ATOM   1211  CG   GLN L 160     -27.352  19.273  79.129  1.00 47.64           C
ATOM   1212  CD   GLN L 160     -27.353  18.619  77.751  1.00 51.42           C
ATOM   1213  OE1  GLN L 160     -26.474  17.841  77.354  1.00 54.61           O
```

Fig. 6a continued      kappa light chain

| | | | | | | | | | |
|---|---|---|---|---|---|---|---|---|---|
| ATOM | 1214 | NE2 | GLN L 160 | -28.351 | 18.941 | 76.956 | 1.00 | 51.87 | N |
| ATOM | 1215 | N | GLU L 161 | -24.947 | 22.884 | 79.252 | 1.00 | 32.26 | N |
| ATOM | 1216 | CA | GLU L 161 | -24.315 | 24.116 | 78.812 | 1.00 | 30.57 | C |
| ATOM | 1217 | C | GLU L 161 | -24.096 | 24.228 | 77.315 | 1.00 | 29.51 | C |
| ATOM | 1218 | O | GLU L 161 | -24.030 | 23.218 | 76.609 | 1.00 | 31.47 | O |
| ATOM | 1219 | CB | GLU L 161 | -22.989 | 24.254 | 79.465 | 1.00 | 31.63 | C |
| ATOM | 1220 | CG | GLU L 161 | -23.068 | 25.232 | 80.584 | 1.00 | 39.52 | C |
| ATOM | 1221 | CD | GLU L 161 | -22.438 | 24.715 | 81.857 | 1.00 | 45.11 | C |
| ATOM | 1222 | OE1 | GLU L 161 | -21.196 | 24.764 | 81.949 | 1.00 | 43.57 | O |
| ATOM | 1223 | OE2 | GLU L 161 | -23.211 | 24.287 | 82.736 | 1.00 | 48.88 | O |
| ATOM | 1224 | N | SER L 162 | -23.964 | 25.449 | 76.818 | 1.00 | 27.95 | N |
| ATOM | 1225 | CA | SER L 162 | -23.733 | 25.712 | 75.415 | 1.00 | 24.52 | C |
| ATOM | 1226 | C | SER L 162 | -22.917 | 27.003 | 75.355 | 1.00 | 23.12 | C |
| ATOM | 1227 | O | SER L 162 | -23.213 | 27.968 | 76.057 | 1.00 | 21.32 | O |
| ATOM | 1228 | CB | SER L 162 | -25.089 | 25.831 | 74.776 | 1.00 | 24.91 | C |
| ATOM | 1229 | OG | SER L 162 | -24.944 | 26.008 | 73.380 | 1.00 | 28.23 | O |
| ATOM | 1332 | N | SER L 176 | -24.700 | 29.533 | 78.016 | 1.00 | 20.73 | N |
| ATOM | 1333 | CA | SER L 176 | -25.984 | 29.359 | 78.650 | 1.00 | 20.18 | C |
| ATOM | 1334 | C | SER L 176 | -25.967 | 28.050 | 79.391 | 1.00 | 19.90 | C |
| ATOM | 1335 | O | SER L 176 | -25.400 | 27.058 | 78.938 | 1.00 | 18.83 | O |
| ATOM | 1336 | CB | SER L 176 | -27.081 | 29.343 | 77.602 | 1.00 | 22.81 | C |
| ATOM | 1337 | OG | SER L 176 | -26.755 | 28.427 | 76.557 | 1.00 | 27.50 | O |
| ATOM | 1338 | N | SER L 177 | -26.543 | 28.045 | 80.570 | 1.00 | 21.10 | N |
| ATOM | 1339 | CA | SER L 177 | -26.716 | 26.843 | 81.325 | 1.00 | 22.83 | C |
| ATOM | 1340 | C | SER L 177 | -28.233 | 26.701 | 81.427 | 1.00 | 24.50 | C |
| ATOM | 1341 | O | SER L 177 | -28.927 | 27.679 | 81.752 | 1.00 | 26.47 | O |
| ATOM | 1342 | CB | SER L 177 | -26.100 | 27.030 | 82.675 | 1.00 | 20.36 | C |
| ATOM | 1343 | OG | SER L 177 | -25.923 | 25.738 | 83.209 | 1.00 | 25.00 | O |
| ATOM | 1344 | N | THR L 178 | -28.783 | 25.535 | 81.113 | 1.00 | 26.21 | N |
| ATOM | 1345 | CA | THR L 178 | -30.193 | 25.289 | 81.284 | 1.00 | 25.67 | C |
| ATOM | 1346 | C | THR L 178 | -30.333 | 24.182 | 82.316 | 1.00 | 26.52 | C |
| ATOM | 1347 | O | THR L 178 | -29.692 | 23.127 | 82.251 | 1.00 | 25.41 | O |
| ATOM | 1348 | CB | THR L 178 | -30.797 | 24.854 | 79.993 | 1.00 | 24.43 | C |
| ATOM | 1349 | OG1 | THR L 178 | -30.504 | 25.890 | 79.065 | 1.00 | 27.73 | O |
| ATOM | 1350 | CG2 | THR L 178 | -32.288 | 24.606 | 80.101 | 1.00 | 23.92 | C |
| ATOM | 1359 | N | THR L 180 | -33.064 | 21.776 | 83.928 | 1.00 | 33.72 | N |
| ATOM | 1360 | CA | THR L 180 | -34.412 | 21.334 | 83.617 | 1.00 | 36.96 | C |
| ATOM | 1361 | C | THR L 180 | -34.895 | 20.441 | 84.742 | 1.00 | 39.75 | C |
| ATOM | 1362 | O | THR L 180 | -34.162 | 19.554 | 85.220 | 1.00 | 40.12 | O |
| ATOM | 1363 | CB | THR L 180 | -34.439 | 20.578 | 82.248 | 1.00 | 37.34 | C |
| ATOM | 1364 | OG1 | THR L 180 | -34.262 | 21.580 | 81.236 | 1.00 | 38.56 | O |
| ATOM | 1365 | CG2 | THR L 180 | -35.746 | 19.829 | 81.975 | 1.00 | 36.31 | C |
| ATOM | 1366 | N | LEU L 181 | -36.102 | 20.772 | 85.213 | 1.00 | 41.45 | N |
| ATOM | 1367 | CA | LEU L 181 | -36.790 | 19.955 | 86.189 | 1.00 | 41.68 | C |
| ATOM | 1368 | C | LEU L 181 | -38.283 | 19.907 | 85.844 | 1.00 | 41.64 | C |
| ATOM | 1369 | O | LEU L 181 | -38.823 | 20.667 | 85.022 | 1.00 | 39.32 | O |
| ATOM | 1370 | CB | LEU L 181 | -36.472 | 20.527 | 87.616 | 1.00 | 41.26 | C |
| ATOM | 1371 | CG | LEU L 181 | -36.887 | 21.835 | 88.321 | 1.00 | 44.99 | C |
| ATOM | 1372 | CD1 | LEU L 181 | -35.940 | 21.997 | 89.487 | 1.00 | 42.76 | C |
| ATOM | 1373 | CD2 | LEU L 181 | -36.694 | 23.093 | 87.505 | 1.00 | 45.40 | C |

Fig 6b kappa heavy chain

| ATOM | 2595 | N | LYS | H | 126 | -39.678 | 16.046 | 64.413 | 1.00 | 20.92 | N |
|------|------|------|-----|---|-----|---------|--------|--------|------|-------|---|
| ATOM | 2596 | CA | LYS | H | 126 | -40.480 | 16.635 | 65.460 | 1.00 | 19.79 | C |
| ATOM | 2597 | C | LYS | H | 126 | -40.194 | 18.131 | 65.371 | 1.00 | 21.17 | C |
| ATOM | 2598 | O | LYS | H | 126 | -39.025 | 18.554 | 65.306 | 1.00 | 23.97 | O |
| ATOM | 2599 | CB | LYS | H | 126 | -40.054 | 16.081 | 66.825 | 1.00 | 18.88 | C |
| ATOM | 2600 | CG | LYS | H | 126 | -41.090 | 16.590 | 67.794 | 1.00 | 26.44 | C |
| ATOM | 2601 | CD | LYS | H | 126 | -40.944 | 16.341 | 69.291 | 1.00 | 32.32 | C |
| ATOM | 2602 | CE | LYS | H | 126 | -41.916 | 17.243 | 70.134 | 1.00 | 37.31 | C |
| ATOM | 2603 | NZ | LYS | H | 126 | -41.584 | 18.677 | 70.172 | 1.00 | 35.44 | N |
| ATOM | 2608 | N | PRO | H | 128 | -40.310 | 22.204 | 66.796 | 1.00 | 18.58 | N |
| ATOM | 2609 | CA | PRO | H | 128 | -39.950 | 22.699 | 68.117 | 1.00 | 19.70 | C |
| ATOM | 2610 | C | PRO | H | 128 | -41.041 | 23.367 | 68.948 | 1.00 | 22.10 | C |
| ATOM | 2611 | O | PRO | H | 128 | -42.127 | 23.691 | 68.475 | 1.00 | 25.30 | O |
| ATOM | 2612 | CB | PRO | H | 128 | -38.769 | 23.602 | 67.812 | 1.00 | 18.78 | C |
| ATOM | 2613 | CG | PRO | H | 128 | -39.053 | 24.200 | 66.457 | 1.00 | 17.91 | C |
| ATOM | 2614 | CD | PRO | H | 128 | -39.898 | 23.122 | 65.749 | 1.00 | 20.81 | C |
| ATOM | 2615 | N | SER | H | 129 | -40.828 | 23.620 | 70.221 | 1.00 | 24.82 | N |
| ATOM | 2616 | CA | SER | H | 129 | -41.770 | 24.395 | 70.995 | 1.00 | 23.50 | C |
| ATOM | 2617 | C | SER | H | 129 | -40.946 | 25.623 | 71.266 | 1.00 | 24.48 | C |
| ATOM | 2618 | O | SER | H | 129 | -39.763 | 25.502 | 71.565 | 1.00 | 22.58 | O |
| ATOM | 2619 | CB | SER | H | 129 | -42.105 | 23.686 | 72.286 | 1.00 | 28.31 | C |
| ATOM | 2620 | OG | SER | H | 129 | -42.934 | 22.546 | 72.073 | 1.00 | 36.78 | O |
| ATOM | 2628 | N | PHE | H | 131 | -40.521 | 28.925 | 73.626 | 1.00 | 30.04 | N |
| ATOM | 2629 | CA | PHE | H | 131 | -41.040 | 29.482 | 74.848 | 1.00 | 27.87 | C |
| ATOM | 2630 | C | PHE | H | 131 | -40.215 | 30.723 | 75.051 | 1.00 | 30.92 | C |
| ATOM | 2631 | O | PHE | H | 131 | -39.007 | 30.683 | 74.789 | 1.00 | 26.23 | O |
| ATOM | 2632 | CB | PHE | H | 131 | -40.810 | 28.570 | 76.022 | 1.00 | 30.11 | C |
| ATOM | 2633 | CG | PHE | H | 131 | -41.537 | 27.235 | 75.970 | 1.00 | 30.98 | C |
| ATOM | 2634 | CD1 | PHE | H | 131 | -42.931 | 27.183 | 75.945 | 1.00 | 30.57 | C |
| ATOM | 2635 | CD2 | PHE | H | 131 | -40.808 | 26.050 | 75.966 | 1.00 | 33.12 | C |
| ATOM | 2636 | CE1 | PHE | H | 131 | -43.590 | 25.948 | 75.915 | 1.00 | 31.13 | C |
| ATOM | 2637 | CE2 | PHE | H | 131 | -41.479 | 24.815 | 75.932 | 1.00 | 33.57 | C |
| ATOM | 2638 | CZ | PHE | H | 131 | -42.863 | 24.765 | 75.907 | 1.00 | 31.34 | C |
| ATOM | 2646 | N | LEU | H | 133 | -38.146 | 33.716 | 77.032 | 1.00 | 38.18 | N |
| ATOM | 2647 | CA | LEU | H | 133 | -37.285 | 33.930 | 78.190 | 1.00 | 34.16 | C |
| ATOM | 2648 | C | LEU | H | 133 | -37.523 | 35.428 | 78.330 | 1.00 | 35.44 | C |
| ATOM | 2649 | O | LEU | H | 133 | -37.005 | 36.294 | 77.609 | 1.00 | 32.35 | O |
| ATOM | 2650 | CB | LEU | H | 133 | -35.823 | 33.622 | 77.863 | 1.00 | 29.24 | C |
| ATOM | 2651 | CG | LEU | H | 133 | -35.533 | 32.258 | 77.309 | 1.00 | 22.14 | C |
| ATOM | 2652 | CD1 | LEU | H | 133 | -34.066 | 32.136 | 77.012 | 1.00 | 23.67 | C |
| ATOM | 2653 | CD2 | LEU | H | 133 | -35.970 | 31.213 | 78.300 | 1.00 | 27.77 | C |
| ATOM | 2749 | N | LEU | H | 150 | -36.371 | 30.246 | 73.846 | 1.00 | 22.90 | N |
| ATOM | 2750 | CA | LEU | H | 150 | -35.971 | 28.876 | 74.075 | 1.00 | 23.38 | C |
| ATOM | 2751 | C | LEU | H | 150 | -36.705 | 28.058 | 73.003 | 1.00 | 25.45 | C |
| ATOM | 2752 | O | LEU | H | 150 | -37.917 | 28.204 | 72.817 | 1.00 | 24.96 | O |
| ATOM | 2753 | CB | LEU | H | 150 | -36.391 | 28.505 | 75.477 | 1.00 | 18.99 | C |
| ATOM | 2754 | CG | LEU | H | 150 | -36.325 | 27.052 | 75.868 | 1.00 | 19.75 | C |
| ATOM | 2755 | CD1 | LEU | H | 150 | -34.917 | 26.528 | 75.789 | 1.00 | 22.45 | C |
| ATOM | 2756 | CD2 | LEU | H | 150 | -36.781 | 26.912 | 77.286 | 1.00 | 19.55 | C |
| ATOM | 2764 | N | LYS | H | 152 | -37.287 | 24.376 | 72.183 | 1.00 | 25.67 | N |
| ATOM | 2765 | CA | LYS | H | 152 | -37.209 | 23.103 | 72.858 | 1.00 | 23.11 | C |
| ATOM | 2766 | C | LYS | H | 152 | -37.793 | 21.909 | 72.110 | 1.00 | 23.19 | C |
| ATOM | 2767 | O | LYS | H | 152 | -38.886 | 21.985 | 71.563 | 1.00 | 22.11 | O |
| ATOM | 2768 | CB | LYS | H | 152 | -37.905 | 23.319 | 74.200 | 1.00 | 25.76 | C |
| ATOM | 2769 | CG | LYS | H | 152 | -37.302 | 22.378 | 75.195 | 1.00 | 29.14 | C |
| ATOM | 2770 | CD | LYS | H | 152 | -37.759 | 22.579 | 76.622 | 1.00 | 30.74 | C |
| ATOM | 2771 | CE | LYS | H | 152 | -36.922 | 21.597 | 77.460 | 1.00 | 28.69 | C |
| ATOM | 2772 | NZ | LYS | H | 152 | -37.314 | 20.228 | 77.199 | 1.00 | 25.73 | N |
| ATOM | 2773 | N | ASP | H | 153 | -37.045 | 20.807 | 72.047 | 1.00 | 25.81 | N |
| ATOM | 2774 | CA | ASP | H | 153 | -37.461 | 19.487 | 71.575 | 1.00 | 22.60 | C |
| ATOM | 2775 | C | ASP | H | 153 | -37.870 | 19.231 | 70.146 | 1.00 | 20.15 | C |
| ATOM | 2776 | O | ASP | H | 153 | -38.939 | 18.761 | 69.803 | 1.00 | 18.56 | O |
| ATOM | 2777 | CB | ASP | H | 153 | -38.561 | 19.010 | 72.523 | 1.00 | 26.65 | C |
| ATOM | 2778 | CG | ASP | H | 153 | -38.083 | 18.807 | 73.962 | 1.00 | 26.68 | C |
| ATOM | 2779 | OD1 | ASP | H | 153 | -36.935 | 18.446 | 74.194 | 1.00 | 28.52 | O |
| ATOM | 2780 | OD2 | ASP | H | 153 | -38.866 | 19.018 | 74.873 | 1.00 | 26.88 | O |

Fig. 6b continued kappa heavy chain

| | | | | | | | | | |
|---|---|---|---|---|---|---|---|---|---|
| ATOM | 2940 | N | PHE | H | 175 | -27.214 | 30.210 | 70.335 | 1.00 23.94 | N |
| ATOM | 2941 | CA | PHE | H | 175 | -26.383 | 29.122 | 70.813 | 1.00 23.42 | C |
| ATOM | 2942 | C | PHE | H | 175 | -26.478 | 27.831 | 69.986 | 1.00 23.74 | C |
| ATOM | 2943 | O | PHE | H | 175 | -27.538 | 27.522 | 69.409 | 1.00 23.81 | O |
| ATOM | 2944 | CB | PHE | H | 175 | -26.758 | 28.815 | 72.248 | 1.00 22.94 | C |
| ATOM | 2945 | CG | PHE | H | 175 | -26.259 | 29.899 | 73.148 | 1.00 20.21 | C |
| ATOM | 2946 | CD1 | PHE | H | 175 | -24.971 | 29.801 | 73.645 | 1.00 19.49 | C |
| ATOM | 2947 | CD2 | PHE | H | 175 | -27.079 | 30.977 | 73.458 | 1.00 20.84 | C |
| ATOM | 2948 | CE1 | PHE | H | 175 | -24.497 | 30.807 | 74.468 | 1.00 20.36 | C |
| ATOM | 2949 | CE2 | PHE | H | 175 | -26.595 | 31.980 | 74.294 | 1.00 22.58 | C |
| ATOM | 2950 | CZ | PHE | H | 175 | -25.300 | 31.901 | 74.800 | 1.00 21.02 | C |
| ATOM | 2951 | N | PRO | H | 176 | -25.360 | 27.078 | 69.878 | 1.00 22.56 | N |
| ATOM | 2952 | CA | PRO | H | 176 | -25.321 | 25.723 | 69.318 | 1.00 19.83 | C |
| ATOM | 2953 | C | PRO | H | 176 | -26.377 | 24.835 | 69.977 | 1.00 21.20 | C |
| ATOM | 2954 | O | PRO | H | 176 | -26.508 | 24.942 | 71.200 | 1.00 22.55 | O |
| ATOM | 2955 | CB | PRO | H | 176 | -23.910 | 25.305 | 69.595 | 1.00 16.67 | C |
| ATOM | 2956 | CG | PRO | H | 176 | -23.083 | 26.559 | 69.637 | 1.00 15.02 | C |
| ATOM | 2957 | CD | PRO | H | 176 | -24.018 | 27.503 | 70.334 | 1.00 17.20 | C |
| ATOM | 2963 | N | VAL | H | 178 | -28.150 | 21.582 | 71.822 | 1.00 22.66 | N |
| ATOM | 2964 | CA | VAL | H | 178 | -27.623 | 20.460 | 72.565 | 1.00 21.24 | C |
| ATOM | 2965 | C | VAL | H | 178 | -28.654 | 19.371 | 72.365 | 1.00 20.88 | C |
| ATOM | 2966 | O | VAL | H | 178 | -29.868 | 19.553 | 72.269 | 1.00 22.54 | O |
| ATOM | 2967 | CB | VAL | H | 178 | -27.441 | 20.749 | 74.109 | 1.00 23.34 | C |
| ATOM | 2968 | CG1 | VAL | H | 178 | -26.426 | 21.863 | 74.326 | 1.00 21.50 | C |
| ATOM | 2969 | CG2 | VAL | H | 178 | -28.744 | 21.171 | 74.737 | 1.00 25.02 | C |
| ATOM | 2970 | N | LEU | H | 179 | -28.110 | 18.208 | 72.193 | 1.00 22.43 | N |
| ATOM | 2971 | CA | LEU | H | 179 | -28.876 | 17.011 | 72.085 | 1.00 25.70 | C |
| ATOM | 2972 | C | LEU | H | 179 | -29.097 | 16.527 | 73.522 | 1.00 25.97 | C |
| ATOM | 2973 | O | LEU | H | 179 | -28.187 | 16.399 | 74.348 | 1.00 25.39 | O |
| ATOM | 2974 | CB | LEU | H | 179 | -28.076 | 16.026 | 71.278 | 1.00 25.57 | C |
| ATOM | 2975 | CG | LEU | H | 179 | -28.702 | 14.674 | 71.023 | 1.00 27.43 | C |
| ATOM | 2976 | CD1 | LEU | H | 179 | -29.897 | 14.757 | 70.074 | 1.00 19.28 | C |
| ATOM | 2977 | CD2 | LEU | H | 179 | -27.587 | 13.805 | 70.469 | 1.00 30.31 | C |
| ATOM | 2978 | N | GLN | H | 180 | -30.365 | 16.320 | 73.815 | 1.00 27.28 | N |
| ATOM | 2979 | CA | GLN | H | 180 | -30.821 | 15.886 | 75.111 | 1.00 25.86 | C |
| ATOM | 2980 | C | GLN | H | 180 | -30.787 | 14.360 | 75.199 | 1.00 26.76 | C |
| ATOM | 2981 | O | GLN | H | 180 | -30.630 | 13.675 | 74.180 | 1.00 27.19 | O |
| ATOM | 2982 | CB | GLN | H | 180 | -32.233 | 16.463 | 75.292 | 1.00 28.23 | C |
| ATOM | 2983 | CG | GLN | H | 180 | -32.316 | 17.984 | 75.105 | 1.00 28.44 | C |
| ATOM | 2984 | CD | GLN | H | 180 | -33.725 | 18.562 | 75.115 | 1.00 31.65 | C |
| ATOM | 2985 | OE1 | GLN | H | 180 | -34.406 | 18.608 | 74.093 | 1.00 30.70 | O |
| ATOM | 2986 | NE2 | GLN | H | 180 | -34.230 | 19.012 | 76.261 | 1.00 30.98 | N |
| ATOM | 2987 | N | SER | H | 181 | -30.940 | 13.753 | 76.391 | 1.00 28.39 | N |
| ATOM | 2988 | CA | SER | H | 181 | -30.945 | 12.305 | 76.549 | 1.00 28.80 | C |
| ATOM | 2989 | C | SER | H | 181 | -32.113 | 11.663 | 75.787 | 1.00 25.40 | C |
| ATOM | 2990 | O | SER | H | 181 | -31.965 | 10.542 | 75.300 | 1.00 28.76 | O |
| ATOM | 2991 | CB | SER | H | 181 | -30.979 | 12.001 | 78.067 | 1.00 31.94 | C |
| ATOM | 2992 | OG | SER | H | 181 | -31.812 | 12.915 | 78.815 | 1.00 40.94 | O |
| ATOM | 2993 | N | SER | H | 182 | -33.258 | 12.324 | 75.579 | 1.00 21.90 | N |
| ATOM | 2994 | CA | SER | H | 182 | -34.325 | 11.787 | 74.720 | 1.00 24.38 | C |
| ATOM | 2995 | C | SER | H | 182 | -33.959 | 11.687 | 73.227 | 1.00 25.28 | C |
| ATOM | 2996 | O | SER | H | 182 | -34.562 | 10.902 | 72.497 | 1.00 29.85 | O |
| ATOM | 2997 | CB | SER | H | 182 | -35.556 | 12.654 | 74.850 | 1.00 17.40 | C |
| ATOM | 2998 | OG | SER | H | 182 | -35.104 | 13.995 | 74.772 | 1.00 19.22 | O |
| ATOM | 3003 | N | LEU | H | 184 | -33.775 | 14.556 | 71.267 | 1.00 20.48 | N |
| ATOM | 3004 | CA | LEU | H | 184 | -34.278 | 15.749 | 70.637 | 1.00 17.63 | C |
| ATOM | 3005 | C | LEU | H | 184 | -33.314 | 16.869 | 71.000 | 1.00 18.68 | C |
| ATOM | 3006 | O | LEU | H | 184 | -32.549 | 16.765 | 71.956 | 1.00 16.48 | O |
| ATOM | 3007 | CB | LEU | H | 184 | -35.675 | 15.980 | 71.168 | 1.00 18.23 | C |
| ATOM | 3008 | CG | LEU | H | 184 | -36.724 | 14.864 | 71.080 | 1.00 12.53 | C |
| ATOM | 3009 | CD1 | LEU | H | 184 | -37.909 | 15.249 | 71.922 | 1.00 10.58 | C |
| ATOM | 3010 | CD2 | LEU | H | 184 | -37.141 | 14.621 | 69.658 | 1.00 13.49 | C |
| ATOM | 3023 | N | SER | H | 186 | -32.310 | 21.176 | 71.626 | 1.00 19.45 | N |
| ATOM | 3024 | CA | SER | H | 186 | -32.755 | 22.411 | 72.223 | 1.00 20.48 | C |
| ATOM | 3025 | C | SER | H | 186 | -31.701 | 23.450 | 71.937 | 1.00 23.05 | C |
| ATOM | 3026 | O | SER | H | 186 | -30.521 | 23.102 | 71.874 | 1.00 25.18 | O |
| ATOM | 3027 | CB | SER | H | 186 | -32.916 | 22.306 | 73.718 | 1.00 21.58 | C |
| ATOM | 3028 | OG | SER | H | 186 | -34.253 | 21.920 | 74.021 | 1.00 32.73 | O |

Fig. 6b continued  kappa heavy chain

```
ATOM   3029  N    LEU H 187   -32.104  24.707  71.768  1.00 21.56      N
ATOM   3030  CA   LEU H 187   -31.233  25.811  71.415  1.00 21.58      C
ATOM   3031  C    LEU H 187   -31.765  27.082  72.120  1.00 23.47      C
ATOM   3032  O    LEU H 187   -32.948  27.118  72.496  1.00 24.42      O
ATOM   3033  CB   LEU H 187   -31.309  25.838  69.897  1.00 19.86      C
ATOM   3034  CG   LEU H 187   -30.875  26.971  69.054  1.00 21.75      C
ATOM   3035  CD1  LEU H 187   -30.413  26.485  67.691  1.00 19.38      C
ATOM   3036  CD2  LEU H 187   -32.048  27.868  68.864  1.00 23.32      C
ATOM   3037  N    SER H 188   -31.014  28.142  72.424  1.00 22.73      N
ATOM   3038  CA   SER H 188   -31.587  29.401  72.873  1.00 21.20      C
ATOM   3039  C    SER H 188   -31.069  30.509  71.988  1.00 20.80      C
ATOM   3040  O    SER H 188   -29.961  30.400  71.441  1.00 21.00      O
ATOM   3041  CB   SER H 188   -31.179  29.775  74.274  1.00 25.10      C
ATOM   3042  OG   SER H 188   -31.586  28.721  75.127  1.00 31.30      O
```

USE OF UREA VARIANTS AS AFFINITY LIGANDS

CROSS REFERENCE TO RELATED APPLICATIONS

This application is a filing under 35 U.S.C. §371 and claims priority to international patent application number PCT/SE2003/001434 filed Sep. 12, 2003, published on May 13, 2004 as WO 2004/039765 and also claims priority to patent application number 0203226-6 filed in Sweden on Oct. 31, 2002 and to patent application number 0203878-4 filed in Sweden on Dec. 20, 2002; the disclosures of which are incorporated herein by reference in their entireties.

TECHNICAL FIELD

The present invention relates to a novel IgG-binding compound useful as a ligand for human IgGs of κ-type and functional derivatives thereof. The invention also relates to a separation matrix for use in affinity chromatography comprising said compound and various uses thereof.

BACKGROUND

Antibodies, also denoted immunoglobulins, are normally synthesised by lymphoid cells derived from B-lymphocytes of bone marrow. Lymphocytes derived from the same clone produce immunoglobulin of a single amino acid sequence. Lymphocytes cannot be directly cultured over long periods of time to produce substantial amounts of their specific antibody. However, a process of somatic cell fusion, specifically between a lymphocyte and a myeloma cell, has been shown to yield hybrid cells that grow in culture and produce a specific antibody known as a monoclonal antibody. The resulting hybrid cell is known as a hybridoma. A monoclonal antibody belongs to a group of antibodies whose population is substantially homogeneous, i.e. the individual molecules of the antibody population are identical except for naturally occurring mutations.

The development of monoclonal antibody technology has provided an enormous opportunity for science and medicine in implementing research, diagnosis and therapy. Monoclonal antibodies are e.g. used in radioimmunoassays, enzyme-linked immunosorbent assays, immunocytopathology, and flow cytometry for in vitro diagnosis, and in vivo for diagnosis and immunotherapy of human disease.

Antibodies are grouped into five different types, namely immunoglobulin G (IgG), which is the most prevalent; immunoglobulin A (IgA); immunoglobulin M (IgM); immunoglobulin D (IgD); and immunoglobulin E (IgE). At present, about thirty percent of the biotechnology-derived drugs under development are based on monoclonal antibodies of type G.

The Y-shaped disposition of the structure of the IgG molecule is well known from standard biochemistry textbooks. In brief, regarding its tertiary structure, one intact IgG molecule consists of six globular regions, each of which is formed by two domains. Regarding its primary structure, an IgG consists of two light chains and two heavy chains, which are covalently linked by disulphide bridges. The two globular parts that correspond to the "base of the Y" form the Fc fragment and are formed by domains consisting of only heavy chain residues. Contrary to this, each of the "arms of the Y" constitutes a Fab fragment with two globular parts each. Each of the globular parts in a Fab fragment is formed when one domain from the light chain contacts one domain from the heavy chain. It is well known that the globular part located further away from the centre of the antibody comprises the regions known as the hypervariable regions as well as the antigen-binding site.

By sequence homology, heavy chains of IgGs can be classified into the four types 1, 2, 3 and 4 whereas light chains fall into two types called λ and κ. In humans, about 40% of the IgG molecules carry a light chain of λ type whereas about 60% carry a light chain of κ type. IgGs built up of both light and heavy chains inherit both types of partitionings. Accordingly, one partitioning divides IgGs into four subclasses IgG1, IgG2, IgG3 and IgG4 as compared to the second partitioning which divides IgGs into two subtypes λ and κ. The same type of classification can be applied to antibody fragments like Fab fragments and so called $F(ab')_2$ fragments, which consist of two Fab fragments connected by a disulphide.

These days, IgGs are generated according to standard techniques in large quantities in cellular expression systems. The most widely used production method includes purification via chromatography, which due to its versatility and sensitivity to the compounds often is the preferred purification method in the context of biomolecules. The term chromatography embraces a family of closely related separation methods, which are all based on the principle that two mutually immiscible phases are brought into contact. More specifically, the target compound is introduced into a mobile phase, which is contacted with a stationary phase. The target compound will then undergo a series of interactions between the stationary and mobile phases as it is being carried through the system by the mobile phase. The interactions exploit differences in the physical or chemical properties of the components in the sample. The interactions can be based on one or more different principles, such as charge, hydrophobicity, affinity etc. In the context of antibodies, affinity chromatography is the most widely utilised purification scheme. More specifically, affinity chromatography is a highly specific mode of chromatography wherein molecular recognition process takes place between a biospecific ligand and a target substance by a principle of lock-key recognition, which is similar to the enzyme binding to a receptor. For a general review of the principles of affinity chromatography, see e.g. Wilchek, M., and Chaiken, I. 2000. An overview of affinity chromatography. *Methods Mol. Biol.* 147: 1-6.

Lawrence et al (J. F. Lawrence, C. Ménard, M-C Hennion, V. Pichon, F. Le Goffic, N. Durand in Journal of Chromatography A, 732 (1996) 277-281: Use of immunoaffinity chromatography as a simplified cleanup technique for the liquid chromatographic determination of phenylurea herbicides in plant material) describes an evaluation of polyclonal antibodies for cleanup of extracts of food samples. More specifically, antibodies were generated in rabbit after inoculations with an antigen prepared from an urea herbicide. Thus, the antibodies were highly specific to the urea herbicide, which is consequently not useful in any method of general antibody purification.

Another application of urea compounds is provided in EP 0 743 067 (Toray Industries), wherein the compounds are presented as highly selective adsorbing materials used for elimination or detoxification of superantigens from body fluids. The superantigens described are enterotoxins and exotoxins, which are large proteins.

In the field of affinity chromatography, various patents and patent applications relate to protein A, which is an IgG-binding cell wall protein of the bacteria *Staphylococcus aureus*, and its use as a ligand. For example, PCT/SE83/00297 (Pharmacia Biotech AB) discloses a recombinant form of protein A, wherein a cysteine residue has been added to the protein A molecule to improve its coupling to a separation matrix for subsequent use as an affinity ligand. Further, U.S. Pat. No. 6,197,927 (assigned to Genentech Inc.) discloses Z domain variants of Staphylococcal protein A exhibiting an IgG-binding capacity equivalent to the wild type Z domain, but a significantly reduced size. However, the binding properties of protein A are not ideal. As is well known, protein A binds to IgG molecules from various mammals, with the highest affinity to the human subclasses of IgG1, IgG2 and IgG4. It binds primarily to a surface formed at the juncture of both the second and the third constant domains, known as CH2 and CH3, of IgG located on the Fc fragment. Consequently, protein A cannot be used in affinity purification of any other fragments of IgG than Fc-containing fragments. In addition, even though protein A binds to some Fab fragments, this binding is not generic, since it targets the variable region. However, the interest in Fab and F(ab')$_2$ fragments has increased lately, since they are smaller than intact IgG molecules but still contain the functional antigen-binding region. Accordingly, the above-mentioned lack of generality becomes another drawback with protein A ligands. Moreover, in attempts to purify IgGs of subclass 3 with protein A-ligands, problems have been reported due to a precipitation of the IgG3 which precipitation is irreversible, thereby causing a loss of purified antibody. Furthermore, protein A exhibits some further drawbacks related to its being a protein. Like most proteins, it is amenable to proteolytic degradation, which may pose serious problems e.g. if a cell lysate is directly applied to a column comprising protein A-based ligand, since most cell lysates will also comprise various proteases. Further, protein A-based ligands are usually labile to the conventionally used cleaning in place (cip) procedures at high pH conditions, which renders reuse of the column more difficult. In addition, protein A-based affinity ligands have also been known to be unstable under acidic conditions, which may result in an undesired leakage of the ligand during the purification process which will both contaminate the product and impair the quality of the purification system.

Another ligand suggested for use in affinity chromatography has been disclosed in U.S. Pat. No. 4,977,247, namely the cell wall protein known as protein G. More specifically, protein G exhibits a different affinity to IgGs as compared to protein A. Protein G binds to a highly conserved region of the constant part of the Fab fragment, primarily to residues from the heavy chain, and consequently it has potential to be used as a generic Fab binder. However, it has been reported that protein G has a reduced binding to Fab fragments of type IgG2. In addition, protein G shares most of the disadvantages of protein-based affinity ligands discussed above in relation to protein A. Furthermore, many of the known protein-based affinity ligands have proven to be relatively expensive to produce.

Consequently, there is a need of novel IgG-binding ligands of a more advantageous nature, which are also more cost-effective to produce. Such new ligands should avoid the above-discussed drawbacks, and preferably also involve more preferable binding properties than the hitherto suggested ligands.

In a recent work by the present inventors, which at the time of filing of the present patent application was still not published, a novel binding site that exhibits the spatial conformation of a pocket was identified. The binding pocket was shown to be specific for human kappa IgGs of all subtypes.

The recently identified binding pocket directed the present inventors to a new target on the human IgG molecule in their efforts to find a new affinity ligand with improved properties as compared to the prior art.

SUMMARY OF THE PRESENT INVENTION

One object of the present invention is to provide a novel ligand to human IgG-molecules of κ-type, which avoids one or more of the above-discussed disadvantages.

A specific object of the present invention is to provide a novel ligand to human IgG-molecules of κ-type, which is general for all subclasses of said IgGs.

Another object of the invention is to provide a novel ligand to human IgG-molecules of κ-type, which is capable of specific binding to said IgGs.

Yet another object of the present invention is to provide a novel ligand to human IgG-molecules of κ-type, which conforms spatially with a binding pocket defined by the amino acids of the interacting surfaces defined in FIG. 2, or with essential parts thereof.

An additional object of the present invention is to provide a novel ligand to human IgG-molecules of κ-type, which exhibits more advantageous chemical properties than protein-based affinity ligands e.g. at extreme pH values and which is more cost-effective to produce.

Further objects and advantages of the present invention will appear from the detailed description that follow below.

BRIEF DESCRIPTION OF THE DRAWINGS

FIG. 3 shows a selection of compounds according to the invention, wherein the substitution pattern has been varied.

FIG. 4 shows orthographic views of some of the compounds derived from AB__0001250.

FIG. 5 A-E show orthographic views of the docked compounds AB__000125[1-5].

FIGS. 6A and B show the structure coordinates of the amino acids that form the interacting surfaces of a binding pocket, which is specific for human IgGs of κ-type. Said binding pocket, and compounds comprising said interacting surfaces, were identified by the present inventors and claimed in a separate patent application, which was still pending, but not public at the time of the present filing.

DEFINITIONS

Figure 1:
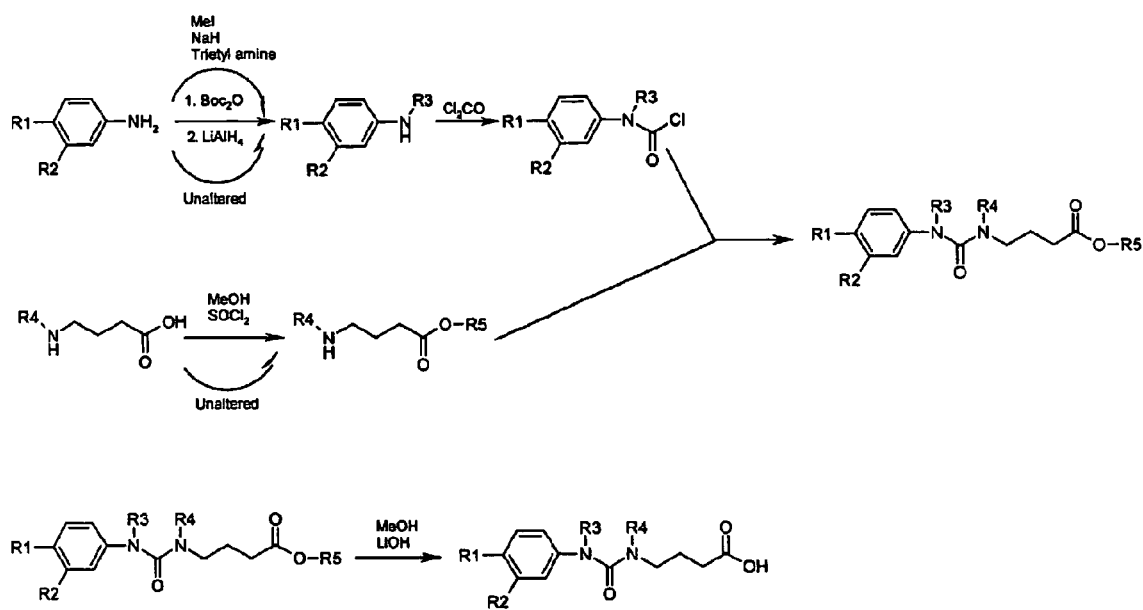
FIG. 1 shows the executed synthetic route to variations of the substitution pattern of a compound according to the invention and also outlines how in the experimental part below, the compounds in the directed library were provided with a handle for immobilisation.

The terms "antibody of κ type", "Fab fragment of κ type" and "F(ab')$_2$ fragment of κ type" mean herein an antibody, a Fab fragment and an F(ab')$_2$ fragment respectively, wherein the light chain is of κ type.

The term "ligand" means herein a chemical entity capable of specific binding to a target.

The term "associating with" refers to a condition of proximity between a chemical entity, or portions thereof, and a target i.e. a binding pocket or binding site on a protein. The association may be non-covalent, wherein the juxta-position is energetically favoured by hydrogen bonding or van der Waals or electrostatic interactions, or alternatively it may be covalent.

The term "functional derivative" is used to mean a chemical substance that is related structurally and functionally to another substance. Thus, a functional derivative comprises a modified structure from the other substance, and maintains the function of the other substance, which in this instance means that it maintains the ability to interact with the same ligands. Thus, a "functional derivative" can be either a natural variation or fragment thereof, or a recombinantly produced entity. In addition, a "functional derivative" can also comprise added molecules or parts, as long as the described function is essentially retained.

The term "binding pocket", as used herein, refers to a region of a molecule or molecular complex, that, as a result of its hollow shape, favourably contributes to the molecule's association with another chemical entity. The term "interacting surface" means herein a surface comprised of residues capable of interacting with a binding molecule or other entity, e.g. by ionic attraction, hydrogen bonds, Van der Waals interaction etc.

The term "strictly conserved" is used herein to mean that after a sequence alignment of all sequences available from an internationally recognised sequence database, the residue type is exactly the same at a specific position for all aligned sequences. An example of such a database is the non-redundant database provided by the National Centre for Biotechnology Information.

The term "structure coordinates" refers to Cartesian coordinates derived from for example mathematical equations related to the patterns obtained on diffraction of a monochromatic beam of X-rays by the atoms (scattering centres) of a protein or protein-ligand complex in crystal form. The diffraction data are used to calculate an electron density map of the repeating unit of the crystal. The electron density maps are then used to establish the positions of the individual atoms of the protein or protein complex.

A "pharmacophore" is defined herein as the assembled atoms or centres in a target molecule, which have critical interactions with a receptor. Some types commonly used include hydrogen bond donors; hydrogen bond acceptors; positively or negatively charged centres; aromatic ring centres; and hydrophobic centres.

The term "docking" means herein a fitting operation, wherein the ability of a chemical entity to bind or "dock" to a binding site is evaluated.

The term "library" means a collection of molecules or other chemical entities with different chemical structures and/or properties.

The term a "Conolly surface" defines the surface of the volume accessible to a hard spherical probe of a given radius, usually taken as 1.4 Å, which is the radius of water in ice form. This surface can be obtained by "rolling the probe" over the atoms of the protein.

DETAILED DESCRIPTION OF THE INVENTION

A first aspect of the present invention is a compound capable of associating with human IgGs of κ-type and functional derivatives thereof. More specifically, the present compound is capable of specific and reversible binding to a binding pocket of a human IgG of κ-type, which binding pocket is defined by the structure coordinates for the amino acids that constitute the interacting surfaces as shown in FIG. 6. Said binding pocket was recently identified by the present inventors, and is located between the two domains (CH1 and CL) of the constant part of κ-Fab. Thus, the herein discussed binding pocket provides a novel binding site for human IgGs of κ-type, which binding site is a general binding site for all such IgGs as well as fragments or functional derivatives thereof.

The present invention is based on an evaluation of a large number of potential binders to κ-Fab of human IgGs, wherein virtual screening hits were tested with NMR. The results from the NMR was subsequently utilised to derive structure-activity relationships that led to the construction of a pharmacophore, and a library of affinity ligands was then designed to optimise binding and include a handle for immobilisation to a chromatographic support. As will be disclosed in detail in the Experimental part below, the present inventors have studied different substitution patterns and evaluated a wide range of structures in order to identify the features required for a compound to exhibit a satisfactory binding to human IgGs of κ-type via the above discussed binding pocket.

More specifically, the compound according to the invention is based on an N,N-alkylated urea moiety located between an aromatic part and an aliphatic part. In the most preferred embodiment, the present invention is an IgG-binding compound represented by formula (I) below

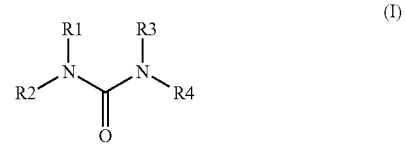

wherein
$R_1$ is $CH_3$ or $CH_2CH_3$;
$R_2$ is a para and/or meta substituted phenyl group;
$R_3$ is H, $CH_3$ or $CH_2CH_3$; and
$R_4$ is a linear or cyclic aliphatic group, which is optionally substituted, or, wherein
$R_1$ and $R_2$ are as stated above while $R_3$ and $R_4$ are both parts the same 4- to 6-membered cyclic entity, which is optionally substituted, and which compound has affinity for human IgG of κ-type.

Thus, in one embodiment, the compound is an affinity ligand with affinity for a Fab fragment of human IgG of κ-type. In some contexts, such an affinity ligand is denoted an affinity adsorbent or an antibody adsorbent.

As the skilled person in this field will easily appreciate, in formula (I), the bonds between the carbonyl carbon and each one of the nitrogen atoms are rotatable. Consequently, position $R_1$ is equivalent to position $R_2$ and position $R_3$ is equivalent to position $R_4$, and the definitions herein will encompass any definition of a compound, wherein $R_1$ has been interchanged with $R_2$ as well as when $R_3$ has been interchanged with $R_4$. Likewise, because of the inherent symmetry around the keto group, the pair $R_1/R_2$ is interchangeable with the pair $R_3/R_4$ so all these definitions are also included.

In an advantageous embodiment of the compound, in formula (I), $R_1$ is $CH_3$.

As mentioned above, in formula (I), $R_2$ is a phenyl group, which may be substituted with one or two halogens, such as F, Cl, Br, or I. Since substituents in ortho position have been observed to have a negative impact on binding, any substituents are present in meta and/or para position. Thus, in a specific embodiment, $R_2$ is substituted with Cl or F in the meta position. In another embodiment, $R_2$ is substituted with Cl in the meta position and F in the para position. In another embodiment, $R_2$ is substituted with F in the meta position and Cl in the para position. In yet another embodiment, $R_2$ is substituted with Cl in meta and para position.

Alternatively, or additionally, the $R_2$ phenyl group is substituted with one or more oxygen-comprising groups. Thus, in one embodiment, $R_2$ is a substituted phenyl group and the substituents are selected from the group that consists of F, Cl, Br, I and OH, preferably F and Cl.

In a specific embodiment, $R_2$ is substituted in the para and/or meta position with a group defined as —O—$R_5$, wherein $R_5$ is $CH_3$ or $CH_2CH_3$, and preferably $CH_3$.

As appears from the modelling described in the experimental part below, when the present compound binds to an IgG molecule, $R_2$ will be located in the inner part of the pocket and hence interact with the inner amino acids of the interacting surfaces of the binding pocket. Larger ring-systems than six-membered rings were according to NMR screening described in the experimental part below found to have a negative influence on binding, and are hence avoided. Also, as mentioned above, in the most preferred embodiment, the aromatic group does not comprise any heteroatoms, since especially the presence of nitrogen atom(s) in the ring has been observed to have a negative impact on binding. However, in an alternative embodiment, the invention is a compound represented by the chemical formula (I) as defined above, wherein $R_2$ is another aromatic group than phenyl. In the most preferred embodiment of this alternative, $R_2$ comprises thiophene.

As mentioned above, $R_3$ can be H or $CH_3$ or $CH_2CH_3$

As mentioned above, in formula (I), $R_4$ can be a linear or cyclic aliphatic group, which is substituted or unsubstituted. In this context, an aliphatic group can be any linear or branched carbon chain interrupted by any heteroatom, as long as the compound fits sufficiently well in the herein-defined binding pocket to provide binding thereof. In one embodiment, the aliphatic chain comprises one or more carbonyl group(s).

In one alternative embodiment, $R_4$ is an aromatic group that comprises a phenyl group. In one embodiment, said phenyl group is substituted in the ortho and/or meta and/or para position. In a specific embodiment, said phenyl group comprises one or more heteroatoms, such as N, S etc.

In a specific embodiment, $R_4$ can be a methyl-substituted amino acid residue, or a derivative thereof. Thus, in a specific embodiment, $R_4$ is selected from the group that consists of aliphatic amino acid residues, hydroxyl-containing amino acid residues, sulphur-containing amino acid residues, aromatic amino acid residues, acidic amino acid residues, basic amino acid residues or imino-containing amino acid residues, or any derivative thereof.

In a specific embodiment, which is especially advantageous if the compound is to be used in a form immobilised to a solid support, e.g. as a ligand in affinity chromatography, the aliphatic group $R_4$ also comprises terminating functionalities useful for such immobilisation. Thus, in one embodiment, an aliphatic group is a linear or branched carbon chain as discussed above, which is terminated with a carboxylic acid i.e. —COOH. In an alternative embodiment, the aliphatic group is terminated with a carboxylic acid derivative, such as an ester, a halide, an amide, a nitrile or the like. In an alternative embodiment, an aliphatic group is a linear or branched carbon chain as discussed above, which is terminated with nitrogen, oxygen, sulphur or any derivative thereof. Such derivatives are well-known to the skilled person in this field, and are also useful for immobilisation. As mentioned above, the only limitation in this context is that the aliphatic group does not impair the binding of the compound to the herein defined binding pocket.

In another embodiment, in formula (I), $R_4$ is $CH_3$. In a specific embodiment, both $R_3$ and $R_4$ are $CH_3$. In a specific embodiment, in formula (I), $R_1$ is $CH_3$; $R_2$ is a phenyl group that has been substituted with Cl in meta and para position; $R_3$ is $CH_3$; and $R_4$ is $CH_3$. In one embodiment, the present compound is selected from the compounds shown in FIG. 3.

As also appears from the above, in an alternative embodiment, $R_3$ and $R_4$ are parts of a 4- to 6-membered cyclic entity. In an advantageous embodiment, the cyclic entity is 3- to 5-membered. Consequently, said cyclic entity comprises the N of Formula (I), $R_3$ and $R_4$ and optionally 1 or 2 other atoms, which may be carbon atoms or heteroatoms. In the most preferred embodiment, the $R_3$ and $R_4$ substituents constitute an amino acid derivative. In one embodiment, $R_3$ and $R_4$ are part of a 5-membered cyclic entity, which in turn is substituted, preferably with a group useful for immobilisation as discussed above. In a specific embodiment, a 5-membered cyclic entity is substituted in the position adjacent to the N with a C(O)—O—CH3 group, and consequently the $R_3$ and $R_4$ substituents of this embodiment are parts of a D-proline derivative. This specific embodiment is denoted AB_0003290 in FIG. 3.

Furthermore, the present invention also encompasses a compound, which is basically represented by formula (I) above, but wherein $R_1$ and $R_3$ are carbon atoms connected to each other to form a cyclic structure. In this embodiment, $R_3$ is a carbonyl group. In this embodiment, $R_4$ is preferably a phenyl group. Thus, this embodiment of the compound is known as 1,3-diphenylimidazolidine-2,4-dione.

In order to provide the best binding to the herein-discussed binding pocket of a human IgG of κ-type, or to a functional derivative thereof, it is preferable that the compound has a non-planar geometry. In the context of the binding pocket, it is noted that the present compound is capable of binding to binding pockets not only of the exact defined structure coordinates as defined herein, but also to pockets defined by interacting surfaces having a mean square deviation from the backbone atoms of the disclosed binding pocket amino acids of not more than 2.0 Å. In a preferred embodiment, said deviation is not more than about 1.5 Å and in the most preferred embodiment, said deviation is not more than 1.0 Å. In one embodiment, the present compound is capable of binding to a human IgG or a functional derivative thereof with a binding constant of at least $10^{-3}$ M, preferably at least $10^{-6}$ M and most preferably at least $10^{-8}$ M. Thus, illustrative intervals of such binding are e.g. $10^{-3}$ M 1 to $10^{-8}$ M, such as $10^{-3}$ $M^{-4}$ to $10^{-6}$M or $10^{-6}$ to $10^{-8}$M.

In a specific embodiment, the present compound is capable of binding to a human IgG of κ-type, or a functional derivative thereof, via a binding pocket formed between two polypeptides, wherein the first polypeptide is the portion of a human IgG κ light chain that starts at one of amino acids 93 to 110 and ends at one of amino acids 187 to 214 of human IgG κ light chain and the second polypeptide is the portion of a human IgG heavy chain that starts at one of amino acids 106 to 128 and ends at one of amino acids 215 to 225 of human IgG heavy chain. In the herein used enumeration of amino acids refers to a human sequence wherein no. 93 is the first amino acid of the constant domain, as also used in FIG. 6.

Thus, the IgG-binding compounds according to the present invention are in general smaller than the prior art affinity ligands used for antibody isolation. In addition, the compounds according to the invention are organic molecules that lack the peptide structure of e.g. protein A- and protein G-based ligands, which in general renders them less susceptible to extreme pH values. Naturally, they are not as susceptible to proteolytic degradation, or any other kind of degradation, as the protein-based prior art ligands either. In addition, the present compounds are more cost-effective to produce.

The compound according to the invention can be prepared by the skilled person in this field using well-known methods, as illustrated e.g. in FIG. 1 below and as explained in the experimental part below under "Synthesis".

A second aspect of the invention is the use of a compound as defined above for selective binding of human IgG of κ-type, or a functional derivative thereof. In the present context, it is understood that the encompassed derivatives can be any human κ-Fab constant part-comprising compounds, i.e. any composition comprising the globular region of an IgG molecule formed by the first constant domain of the heavy chain (CH1) and the constant domain of the light chain (CL). Thus the term includes any of the following terms which are well known from standard IgG terminology: Intact IgG molecules, F(ab')$_2$ fragments, Fab' fragments, Fab fragments and by definition the globular region named itself, all of which have human sequences and light chains of κ-type. This definition includes also any modifications of named IgG or named antibody fragments including even chimeric molecules formed in one part of one of said compositions and in another part of any of the following proteins, peptides, carbohydrates, lipids or any other organic or inorganic entity and chimeric combinations thereof and also any of the above-mentioned covalently attached to solid phase.

The present invention also encompasses a sorption complex comprised of a compound as defined above directly linked to the Fab fragment of a human IgG of κ-type, or a functional derivative thereof. More specifically, the compound is linked to the Fab fragment of said antibody, and more specifically to the herein described binding pocket. Such a sorption complex will form as the compound according to the invention is contacted with a solution comprising human IgG's of κ-type, or a functional derivative thereof, under suitable conditions. The skilled person in this field can easily select such conditions and adjust pH, ionic strength etc to provide or to break up the complex.

Another aspect of the invention is a separation matrix for use in affinity chromatography, wherein the ligands comprises at least one compound as defined above. In a specific embodiment, the ligands have been coupled to a support via linkers. The present matrix can e.g. be in the form of separate particles, preferably porous and essentially spherical particles; a monolith; or a membrane.

The present invention also encompasses a system suitable for affinity chromatography, which is comprised of a separation matrix as defined above packed in a column. The column may be of a size suitable for analytical scale or for large scale chromatography.

Suitable support materials are well known. In one embodiment, the support is a natural polymer, such as agarose, alginate, carrageenan, gelatine etc. Such natural polymers are known to form physically cross-linked networks spontaneously on cooling or on addition of divalent metal ions, and chemical cross-linkers can be added if desired. This kind of supports is easily prepared according to standard methods, such as inverse suspension gelation (S Hjertén: Biochim Biophys Acta 79(2), 393-398 (1964). In another embodiment, the support is comprised of cross-linked synthetic polymers, such as styrene or styrene derivatives, divinylbenzene, acrylamides, acrylate esters, methacrylate esters, vinyl esters, vinyl amides etc. Such polymers are also easily produced according to standard methods, see e.g. "Styrene based polymer supports developed by suspension polymerization" (R Arshady: Chimica e L'Industria 70(9), 70-75 (1988)). Thus, in summary, the support material can in principle be any material that allows the covalent coupling of the IgG-binding compound discussed above, such as the above-discussed polymers, inorganic materials, such as silica, ceramics etc.

Many well-known methods are available for immobilising ligands to a support through suitable functional groups. As the skilled person in this field will realise, the exact choice of coupling method will depend on the structure of the ligand to be immobilised. In one embodiment, the support has hydrophilic surfaces, and if porous, the surfaces of the pores are also hydrophilic. This is advantageous in order to avoid or at least reduce any non-specific protein interactions. It is also advantageous if the surfaces have a high density of groups available for coupling of ligands. Such coupling groups are commonly hydroxyl groups, but may also be allyl groups i.e. double bonds available for grafting, amines, thiols, epoxides and the like. If the support material has undesirable surface properties, it is possible to coat it with a hydrophilic polyhydroxy-functional material before coupling the ligand. The techniques and considerations for coupling of affinity ligands to a suitable support to prepare a separation matrix are well known in this field, see e.g. WO 98/33572 for a detailed review of coupling chemistry as well as suitable linking molecules, therein denoted "extenders".

Another aspect of the invention is a generic method of isolating or separating a target compound, i.e. a human IgG of κ-type, or a functional derivative thereof, from other components in a liquid, wherein a compound or a separation matrix as defined above is used. In the context of immunology, the separation matrix is often denoted an "immunsorbent". In the most preferred embodiment, the present method is affinity chromatography, which is a widely used and well-known separation technique. In brief, in a first step, a solution comprising the desired antibodies is passed over a separation matrix under conditions allowing adsorption of the antibody to ligands present on said matrix. Such conditions are controlled e.g. by pH and/or salt concentration i.e. ionic strength in the solution. Care should be taken not to exceed the capacity of the matrix, i.e. the flow should be sufficiently slow to allow a satisfactory adsorption. In this step, other components of the solution will pass through in principle unimpeded. Optionally, the matrix is then washed, e.g. with an aqueous solution, in order to remove retained and/or loosely bound substances. In a next step, a second solution denoted an eluent is passed over the matrix under conditions that provide desorption i.e. release of the desired antibody. Such conditions are commonly provided by a change of the pH, the salt concentration i.e. ionic strength, hydrophobicity etc. Various elution schemes are known, such as gradient elution and stepwise elution. Elution can also be provided by a second solution comprising a competitive substance, which will replace the desired antibody on the matrix.

In an alternative embodiment, the compound according to the invention is used in site-specific modification of a human IgG of κ-type, or a functional derivative thereof. More specifically, a human IgG of κ-type, or a functional derivative thereof, can be modified by binding a compound as defined above selectively to the binding pocket identified by the present inventors. In a specific embodiment, the modification is a stabilisation of Fab-folding.

In an alternative embodiment, the present compound is used in an immunological assay for detection of a human IgG of κ-type, or a functional derivative thereof. In this case, the compound is preferably labelled with a suitable detectable label as conventionally used, such as a fluorescent label, a luminescent label, a chemiluminiscent label, an enzyme label, a radioactive label, an absorbance label etc. Such assays may be in solution or on solid phase. In one embodiment, the human κ-Fab constant part-comprising composition is a human IgG or a fragment thereof. In the preferred embodiment, the present assay is a competitive assay, wherein the ability of a candidate ligand to displace a known ligand's binding to a compound or binding pocket as defined above is evaluated.

DETAILED DESCRIPTION OF THE DRAWINGS

FIG. 1 shows the executed synthetic route to i) variations of the substitution pattern and ii) provide the compounds in the directed library with a handle for immobilisation as discussed below in Example 2. To the top-left, the original hit AB_0001250 is shown. The synthesis will be described in detail below in the section Materials and methods.

Figure 2:
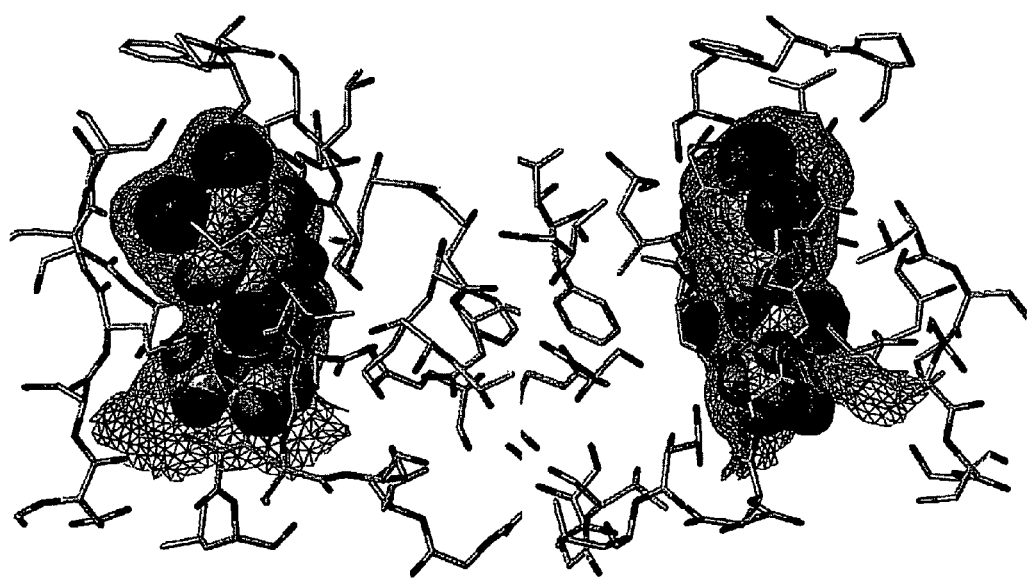
FIG. 2 shows orthographic views of the herein-discussed binding pocket in chicken net model.

FIG. 2 shows orthographic views of the herein-discussed binding pocket in chicken net model. The amino acid residues forming the pocket are shown in stick model and the corresponding structure coordinates are presented in FIG. 6. Docked hit AB_0001250 is shown in space-fill model to illustrate the possibilities of the pocket to harbour a substituted phenyl ring.

FIG. 3 shows a selection of compounds according to the invention, wherein the substitution pattern of $R_1$, $R_2$ as well as $R_3$ and $R_4$ has been varied. A central N,N-alkylated urea moiety as well as a para and/or meta substituted phenyl groups are present in all the compounds.

FIG. 4 shows orthographic views of compounds derived from AB_0001250. Five docked hits superimpose very well onto the original hit AB_0001250.

FIG. 5 A-E show orthographic views of the docked compounds AB_000125[1-5] in the binding pocket, as discussed in more detail in the experimental part below.

FIGS. 6 A and B show the structure coordinates of the amino acids that form the interacting surfaces of the binding pocket shown in FIG. 2, which is specific for human IgGs of κ-type. FIG. 6A shows the coordinates of the light chain, while FIG. 6B shows the heavy chain. More specifically, the structure coordinates shown form a small pocket in between the two domains (CH1 and CL) of the constant part of κ-Fab and constitutes a novel target binding site. The residues forming the pocket together with some residues located at the entrance and contributing significantly to the topology of the putative binding site have been identified as follows. From the light chain, there are Q124, S127, G128, T129, S131, V133, G157, N158, S159, Q160, E161, S162, S176, S177, T178, T180, L181, and they are all strictly conserved for all sequences of κ-type identified in a sequence homology search. The residues from the heavy chain are K126, P128, S129, F131, L133, L150, K152, D153, F175, P176, V178, L179, Q180, S181, S182, L184, S186, L187 and S188, bold being strictly conserved and remaining highly conserved. The structure coordinates of the full amino acid sequence of a human IgG of κ-type can be obtained from the Protein Data Bank, accession code 1vge, e.g. at—http://www.rcsb.org/pdb/.

Figure 7:
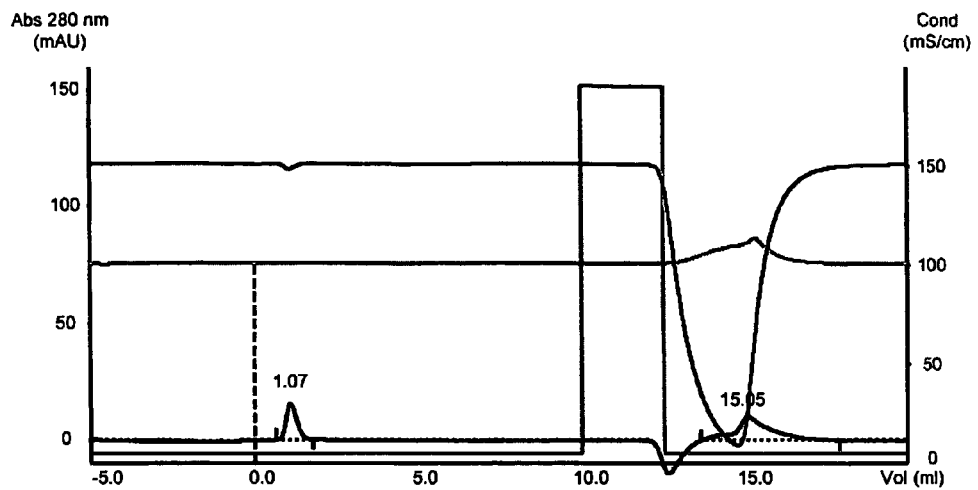
FIG. 7 shows the results of affinity chromatography on a separation matrix according to the invention, wherein a Fab-fragment of κ-type is successfully isolated.

FIG. 7 illustrates how a Fab-fragment of a monoclonal antibody of kappa-type can be isolated by affinity chromatography using a separation matrix according to the invention, as described in Example 6 below. Injection of the monoclonal ABFab-K1 on the AB_0003291-containing medium according to the invention in PBS, 1 M $(NH_4)_2SO_4$, pH 7 at 0 ml. Cleaning in place (CIP) starts at 10.0 ml. The small peak at 1.07 ml is due to injection effect. The protein is not totally removed from the column during the CIP. Evidently, the affinity column is able to bind the monoclonal ABFab-K1.

Figure 8:
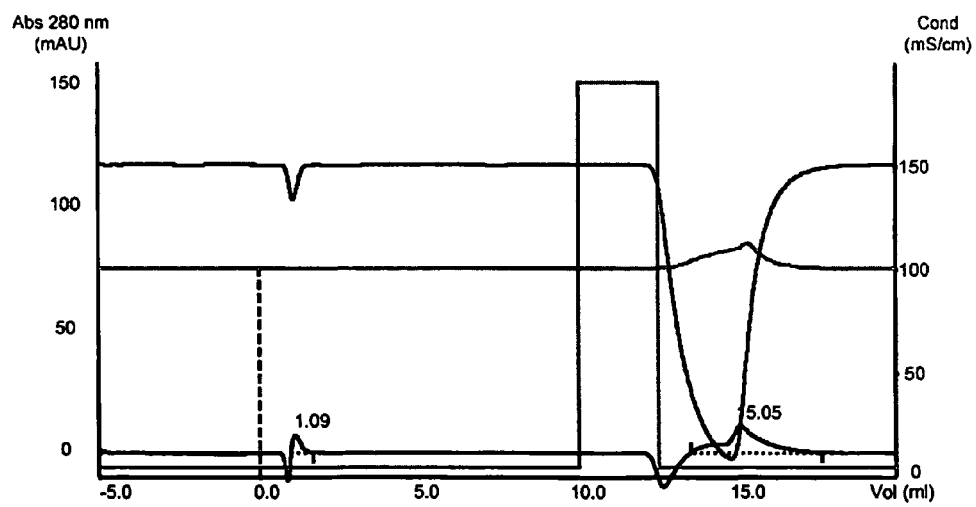
FIG. 8 shows the results of affinity chromatography on a separation matrix according to the invention, wherein another Fab-fragment of κ-type is successfully isolated.

FIG. 8 illustrates how another Fab-fragment of a monoclonal antibody of kappa-type can be isolated by affinity chromatography using a separation matrix according to the invention, as described in Example 6 below. Injection of the monoclonal ABFab-K2 on the AB_0003291-containing media in PBS, 1 M $(NH_4)_2SO_4$, pH 7 at 0 ml. CIP starts at 10.0 ml. The small peak at 1.09 ml is due to injection effect. The protein is not totally removed from the column during the CIP. Evidently, this affinity column is also able to bind the monoclonal ABFab-K2, and the compound according to the invention can consequently be described as a ligand useful as a general binder of human IgG Fab fragments of κ-type.

Figure 9:
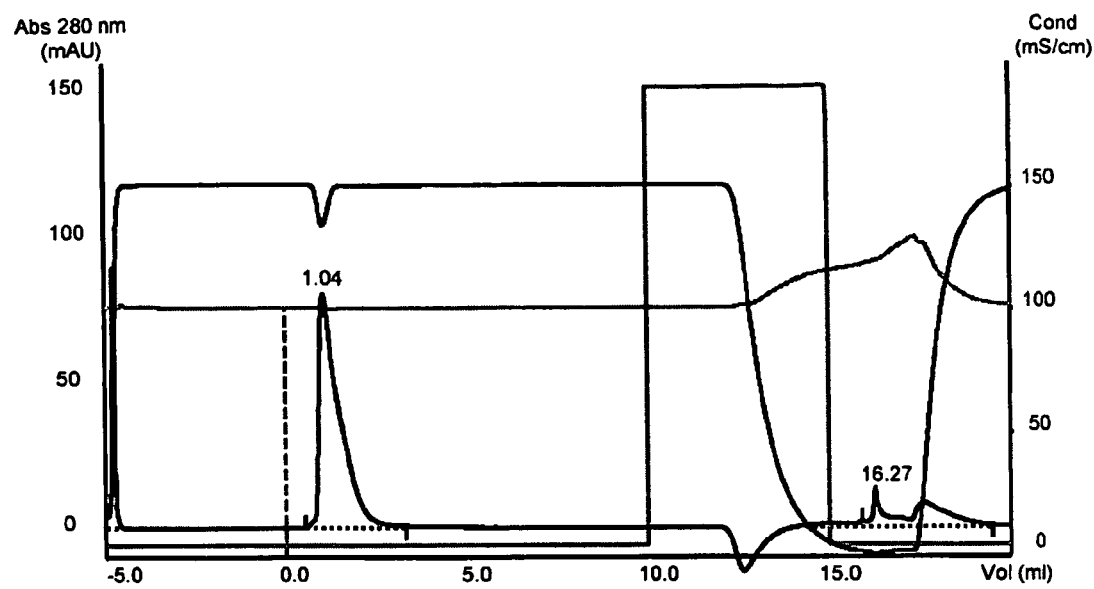
FIG. 9 shows as a comparative test an attempt to isolate a Fab-fragment of lambda-type by affinity chromatography on a separation matrix according to the invention.

FIG. 9 illustrates as a comparative test how a Fab-fragment of a monoclonal antibody of lambda-type is tested in affinity chromatography on a separation matrix according to the invention, as described in Example 6 below. Injection of the monoclonal ABFab-L2 on the AB_0003291-containing media in PBS, 1 M $(NH_4)_2SO_4$, pH 7 at 0 ml. CIP starts at 10.0 ml. From this figure, it clearly appears that the ABFab-L2 directly comes off the affinity column and is found in the flow-through. Accordingly, the separation matrix according to the invention is not suitable for isolation of Fab-fragments of lambda-type, and confirms the statement above that the compound according to the invention is a binder of human IgG Fab fragments of κ-type, but not of lambda-type.

EXPERIMENTAL PART

Below, the present invention will be explained in more detail by way of examples, which however are not to be construed as limiting the present invention as defined by the appended claims. All references given below and elsewhere in the present specification are hereby included herein by reference.

Materials and Methods

Molecular Modelling

Compounds of the directed library were sketched with MDL ISIS/draw and transferred to an OCTANE™ (Silicon Graphics Inc.®) workstation provided with two 195 MHz R10000 processors. The program package SYBYL® (Tripos Inc., 2000) was used for all remaining modelling.

Preparation of Compounds for Docking

The structures of the compounds were transformed into 3D using the program CONCORD and ionised to reflect their most probable protonation state at pH 7. The coordinates were then subject to 500 cycles of minimisation using the MMFF94 force field (Halgren 1996—Halgren, T. 1996. Merck molecular force field. I. Basis, form, scope, parameterisation, and performance of MMFF94. *J. Comp. Chem.* 17: 490-519.).

Docking of Prepared Molecules

Docking simulations have been performed with the program FlexX™ (Rarey et al. 1996 Rarey, M., Kramer, B., Lengauer, T., and Klebe G. 1996. A fast flexible docking method using an incremental construction algorithm. *J. Mol. Biol.* 261: 470-489.) which is part of the SYBYL package. FlexX allows flexibility in the ligands, keeping the receptor fixed. All the relevant receptor information necessary for the docking simulations is stored in the receptor definition file (rd file). FlexX uses formal charges, which were turned on during the docking simulations. The protein structure used was the highest-resolution (2.0 Å) crystal structure of κ-Fab (accession code to the Protein Data Bank 1vge, Chacko et al., 1996 Chacko, S., Padlan, E. A., Portolano, S., McLachlan, S. M., Rapoport, B.: Structural studies of human autoantibodies.

Crystal structure of a thyroid peroxidase autoantibody Fab. *J Biol Chem* 271 pp. 12191 (1996)). The following residues were included in the definition of the binding site: from the light chain: Ser-131, Val-133, Ser-159, Gln-160, Glu-161, Ser-162, Ser-176, Thr-178, and Thr-180. From the heavy chain: Leu-150, Lys-152, Phe-175, Pro-176, Val-178, Gln-180, Ser-186, Leu-187, Ser-188. All of these residues have previously been shown by the present inventors to be strictly conserved as observed from a sequence alignment and are a subset of the identified pocket. The subset was created by taking all residues with at least one atom at a distance of at least 4 Å from the docked hit AB_0001250 and subsequently by including some additional residues to complete a Conolly surface of the pocket surrounding the docked hit. In the protein structure, the $\epsilon$ carbonyl oxygen of H:Gln-180 is located 2.5 Å away from one of the $\delta$ carboxyl oxygens of H:Asp153. This was assumed to be an error due to misinterpretation of the electron density of the carboxyamide terminal group of H:Gln-180, and the group was consequently flipped around 180°. In this corrected structure, the $\epsilon$ nitrogen of Gln-180 from the heavy chain is at favourable hydrogen bonding distance to the carboxyl oxygen of H:Asp153. Otherwise, defaults have been used when creating the rd file and no special customisations have been done. When necessary the SYBYL LINE NOTATION (sin) core option of FlexX in SYBYL was applied to bias the docking towards conformations that were compatible with the expected binding mode with the phenyl ring inside the pocket. The sin core option was applied with input N(C(NCH3)=O)(C[9]:CH:CH:C:C:CH:@9)CH3 to indicate to the program to start fragment build-up using a common substructure of the six compounds in the directed library. Prior to docking, all water molecules were removed. The 30 best ranked conformations and their FlexX score were saved for each molecule.

Synthesis of Library Based on AB_0001250

Synthesis of 4-(methylamino) butyric acid methyl ester 4-(methylamino) butyric acid HCl was dissolved in methanol and thionyl chloride in catalytic amount was added drop by drop. The reaction mixture was stirred at 0° C. for 30 min. Thereafter, the solvent was reduced in vacu, yielding a white solid.

Synthesis of 3,4-dichloro-/(N-methyl)-aniline 3,4-dichloro aniline (40 mmol, 5 g) was dissolved in 400 mL of DCM. To this solution was added iodo methane (40 mL), triethyl amine (5 mL), and NaH (40 mmol, 3.8 g). The resulting mixture was stirred at ambient temperature over night, where after small aliquots of water summing up to a total of 50 mL of water was added, followed of an additional hour of stirring. The reaction mixture was transferred to a separation funnel and extracted with 5% sodium thio-sulphate, dried over magnesium sulphate and concentrated in vacu to almost complete dryness. The material was separated by silica chromatography (pentane:ether—8:2), the appropriate fractions were collected and concentrated in vacu to almost complete dryness, yielding 3 g of material including some solvent. The correct material was indicated by LC-MS analysis. This material was directly used in the subsequent step.

General Method for Synthesis of N-methylated Aniline Derivatives

The aniline derivative was dissolved in DCM and sodium hydride (in the case of AB_0001253 sodium bis(trimethylsilyl) amide) (1.5 eq) and di-tertbutyl-di-carbonate (1.3 eq) was added followed by stirring at room temperature over night. The reaction mixture was transferred to a separatory funnel and extracted with water, dried over magnesium sulphate, and concentrated in vacu. The crude product was dissolved in THF and lithium alumina hydride (1.2-2 eq) was added and the reaction mixture was refluxed until completion as indicated by LC-MS. Thereafter the mixture was filtered. This filtrate was used directly in the subsequent step.

General Method for Synthesis of Urea Derivatives

To a THF solution of the N-methylated aniline (or the non-N-methylated aniline derivative) was added phosgene (20% in toluene) in large excess and the reaction mixture was stirred at room temperature for 30 min, concentrated in vacu, and re-dissolved in DCM. To this solution was added an excess of triethyl amine and 4-(methylamino) butyric acid methyl ester (or 4-amino butyric acid methyl ester) (approx. 1 eq). The reaction mixture was stirred at room temperature for 3 hours, concentrated in vacu, and purified by RP-HPLC.

General Method for Hydrolysis of Methylesters

The methyl ester of the urea derivative (0.5 g) was dissolved in methanol (10 mL) and lithium hydroxide (0.25 g) was added. The resulting mixture was stirred at ambient temperature for 5 hours, neutralised with 1 M HCl, and concentrated in vacu. The resulting material was purified by RP-HPLC.

Synthesis of 1-(3,4-dichlorophenyl)-1,3-dimethyl-3-butyric acid urea 3,4-dichloro-N-methyl-aniline (all material from previous description) was dissolved in 200 mL of DCM. To the solution was added phosgene (20 mL, 20% sol. in toluene) and the mixture was stirred for 30 minutes at ambient temperature. The solvent was removed in vacu and an additional 100 mL of DCM was added, followed by removal of the added solvent in vacu.

The remaining solid was dissolved in 200 mL of DCM and 4-methyl-4-amino butyric acid (2 g) was added followed by the addition of triethyl amine (5 mL). The resulting mixture was stirred at ambient temperature during 2 hours. Thereafter, the reaction mixture was transferred to a separation funnel and partitioned between DCM and water. The organic phase was isolated, dried over magnesium sulphate, and concentrated in vacu. The remaining material was purified by silica column chromatography (DCM:Et-OH—9:1), the appropriate fractions were collected and concentrated in vacu to yield 1.4 g of the desired material as a clear oil.

EXAMPLE 1

Binding Test Using NMR

All NMR experiments were performed at 298 K on a Bruker Avance 500 MHz spectrometer. The 1D saturation transfer difference method (STD-NMR) was used as screening assay (Mayer M. and Meyer B. 1999. Characterisation of Ligand Binding by Saturation Transfer Difference NMR Spectroscopy. Angew. Chem., Int. Ed. 38: 1784-1788). The resulting STD-NMR spectrum shows the difference between spectra recorded with on- and off-resonance irradiation of the protein, respectively. The two spectra are recorded in the same experiment in an interleaved fashion. If the resulting STD-NMR spectrum shows the same signals as the reference $^1$H-NMR spectrum of the ligand the result is regarded as positive i.e. the ligand must have contacted the protein. Ligands that do not have any contact with the protein or are very tightly bound to the protein will not give any signal in the resulting STD-NMR spectrum. It has been shown that the method is capable of detecting ligands with dissociation constants between $10^{-3}$ and $10^{-8}$ M (Mayer M. and Meyer B. 1999. Characterisation of Ligand Binding by Saturation Transfer Difference NMR Spectroscopy. *Angew. Chem, Int. Ed.* 38: 1784-1788). The strength of the STD-NMR signal depends upon several factors including protein size, offset and duration of the on-resonance irradiation, the dissociation rate constant and the excess of ligand. The STD-NMR method is advantageous in that the detection limits can be tuned for binding by varying the protein concentration while keeping the ligand concentration constant. Under such conditions, at higher protein concentrations the weak to medium binders are detected, whereas at lower protein concentrations only medium binders are detected. For instance, it has been shown before for another enzyme system that both μM and mM binders were detected at a protein concentration of 35 μM whereas only μM binders were detected at protein concentrations of 1 μM and 100 nM (Peng J. W., Lepre C. A., Fejzo J., Abdul-Manan N. and Moore J. M. 2001, Nuclear Magnetic Resonance-Based Approaches for Lead Generation in Drug Discovery, Methods in Enzymology. 338: 202-230). It should be noted that the signal intensity at one specific protein concentration should not be taken as a direct measure of the binding strength. For instance, in the same study, a mM binder showed a stronger signal as compared to a μM binder at 35 μM protein concentration whereas when the protein concentration was reduced to 1 μM the signal from the weaker binder vanished. On the other hand the signal of the μM binder became even stronger than before (Peng J. W., Lepre C. A., Fejzo J., Abdul-Manan N. and Moore J. M. 2001, Nuclear Magnetic Resonance-Based Approaches for Lead Generation in Drug Discovery, Methods in Enzymology. 338: 202-230).

Here, three different antibody concentrations were used, namely, 0.5 μM, 100 nM and 20 nM. The antibody used was a human Fab of κ-type. In all cases ligands were tested one-by-one. On-resonance irradiation was set at 0 ppm and off-resonance irradiation was set at 40 ppm. Irradiation time in each scan was 2 s and 16K data points were collected with 1024 scans in total. Compounds for testing were dissolved in $DMSO_{d6}$ to a concentration of 50 mM and 5 μL of the concentrated ligand solution was added to 495 μL buffer solution. The samples thus consisted of 0.5 mM ligand, 20 mM phosphate buffer, 100 mM NaCl and 5% $DMSO_{d6}$ in $D_2O$ at pD 7.5, uncorrected reading on pH-meter. Compounds were initially tested for binding with 0.5 μM antibody. Interesting ligands were further tested with protein concentrations of 100 or 20 nM. A one-dimensional $^1$H-spectrum was acquired first as reference spectrum and subsequently a saturation transfer difference (STD) spectrum was acquired. Each analysis took 60 minutes on the spectrometer.

The results are shown in Table 1 below, wherein the results from NMR screening are compiled.

TABLE 1

Results from the NMR screening

| ID | Chemical name | conc 1 | conc 2 | conc 3 | ctrl |
|---|---|---|---|---|---|
| AB_0000510 | alpha-pyridoin | 0 | | | |
| AB_0000530 | 1-(3-chlorophenyl)-3-methyl-2-pyrazolin-5-one | 0 | | | |
| AB_0000540 | 1,3-diphenylparabanic acid | 0 | | | |
| AB_0000580 | n1-(3-chloro-4-fluorophenyl)-2-[(4,6-dimethylpyrimidin-2-yl)thio]acetamide | 1 | 0 | | |
| AB_0000600 | 3-phenyl-1,2,4-benzotriazine | 1 | 1 | | 0 |
| AB_0000610 | 2-(4-chlorophenyl)-2,3-dihydro-1h-pyrrolo[3,4-c]pyridine-1,3-dione | 0 | | | |
| AB_0000630 | n1-(2,3,4-trifluorophenyl)-2-(1,2,4-oxadiazol-3-yl)acetamide | 0 | | | |
| AB_0000670 | methyl n-[(5-methyl-4-phenyl-1,3-oxazol-2-yl)carbonyl]carbamate | 2 | 0 | | |
| AB_0000690 | n1-(2,4-difluorophenyl)-2-(1,2,4-oxadiazol-3-yl)acetamide | 0 | | | |
| AB_0000700 | 3,6-di-2-pyridyl-1,2,4,5-tetrazine | 0 | | | |
| AB_0000730 | 2-benzylidene-1,3-indandione | 0 | | | |
| AB_0000740 | 5-phenyl-1,2,4-oxadiazol-3-yl n-(4-fluorophenyl)carbamate | 0 | | | |
| AB_0000750 | n-(5,5-dimethyl-7-oxo-4,5,6,7-tetrahydro-benzothiazol-2-yl)-nicotinamide | 0 | | | |
| AB_0000760 | 5-(2-phenyl-1,3-thiazol-4-yl)-1,3,4-oxadiazol-2-ylhydrosulfide | 1 | 0 | | |
| AB_0000790 | 3-[2-oxo-2-(2-pyridyl)ethyl]-1,3-dihydroisobenzofuran-1-one | 0 | | | |
| AB_0000810 | 2-phenoxy-2-phenyl-1-ethanol | 2 | 1 | | 0 |
| AB_0000860 | 1,3-diphenylimidazolidine-2,4-dione | 2 | 2 | 1 | 0 |
| AB_0000880 | 5-bromo-3-phenyl-thiazolidine-2,4-dione | 0 | | | |
| AB_0000900 | 1-(2-naphthoyl)imidazole | 0 | | | |
| AB_0000910 | 3-bromo-4-methoxyphenylacetone | 2 | 2 | 0 | 0 |
| AB_0000930 | 3-chloro-1-phenyl-pyrrole-2,5-dione | 0 | | | |
| AB_0000990 | 3-butyl-2-hydroxy-4h-pyrido[1,2-a]pyrimidin-4-one | 0 | | | |

TABLE 1-continued

Results from the NMR screening

| ID | Chemical name | conc 1 | conc 2 | conc 3 | ctrl |
|---|---|---|---|---|---|
| AB_0001000 | 3-(benzylamino)-1,1,1-trifluoro-2-propanol | 1 | 0 | | |
| AB_0001010 | 2-[5-(2-fluorobenzoyl)-2-thienyl]acetonitrile | 2 | 2 | 2 | 1 |
| AB_0001020 | 5-(3,5-difluorobenzyl)-3-(2-thienyl)-1,2,4-oxadiazole | 1 | 0 | | |
| AB_0001030 | 2-chloro-3-(trifluoromethyl)benzaldehyde | 1 | 0 | | |
| AB_0001040 | 2-hydroxy-3-(2-methyl-1-propenyl)-1,4-naphthoquinone | 1 | 1 | | 0 |
| AB_0001060 | 2-(2-imino-thiazol-3-yl)-1-naphthalen-2-yl-ethanone | 2 | 0 | | |
| AB_0001070 | imiloxan hydrochloride | 1 | 1 | | |
| AB_0001080 | 2-(benzylthio)-5-methyl-4,5-dihydro-1h-imidazol-3-ium chloride | 0 | | | |
| AB_0001090 | n-(3-chlorophenyl)-maleimide | 1 | 0 | | |
| AB_0001100 | ethyl 4-oxo-1,4-dihydroquinoline-3-carboxylate | 0 | | | |
| AB_0001130 | 3-amino-n-[2-(methylthio)ethyl]-4-oxo-3,4-dihydroquinazoline-2-carboxamide | 0 | | | |
| AB_0001150 | 1-[(3,4-dichlorobenzyl)oxy]-1h-imidazole | 2 | 0 | | |
| AB_0001170 | 3-[(2,4-dichlorobenzyl)amino]-1,1,1-trifluoro-2-propanol | 0 | | | |
| AB_0001180 | 3-oxo-2-phenyl-2,3-dihydro-4-pyridazinecarboxylic acid | 0 | | | |
| AB_0001190 | 4-[1-(2-phenylethyl)-(1h)-pyrazol-4-yl]pyridine | 2 | 0 | | |
| AB_0001200 | methyl 1-hydroxy-2-naphthoate | 1 | 0 | | |
| AB_0001220 | 1-(3-trifluoromethyl-phenyl)imidazole | 2 | 0 | | |
| AB_0001230 | (2-naphthoxy)acetic acid, n-hydroxysuccinimide ester | 0 | | | |
| AB_0001240 | methyl 3-(5-chloro-2-methoxyphenyl)-2,3-epoxypropionate | 1 | 1 | | 0 |
| AB_0001250 | 1-(3,4-dichlorophenyl)-1,3,3-trimethylurea | 2 | 2 | 1 | 0 |
| AB_0001260 | 2-pyridyl 2-(2,3-dihydro-1,4-benzodioxin-2-yl)-1,3-thiazole-4-carbothioate | 0 | | | |
| AB_0001270 | 1-[(4-chlorobenzyl)amino]-3-(phenylthio)propan-2-ol | 1 | 0 | | |
| AB_0001290 | 3-[(4-chlorophenoxy)methyl]-5-[(2-pyridylthio)methyl]-1,2,4-oxadiazole | 2 | 1 | | 0 |
| AB_0001300 | 3-(2-thienylcarbonyl)-4h-pyrido[1,2-a]pyrimidin-4-one | 1 | 0 | | |

Concentration code as follows: conc. 1 means 500, conc 2 100 and conc 3 20 nM protein.
NMR signal code: 0 no, 1 weak and 2 strong signal.

As regards table 1, one compound (Compound AB_0001010) showed a positive NMR signal even in the absence of target antibody. That compound is likely to be a false positive and was therefore excluded from further analysis. A total of 22 compounds did not show any binding signal in the NMR experiments performed at highest antibody concentration and were thus designated as non-binders. From 23 compounds which showed signal at the highest antibody concentrations a total of 14 did not show any signal at the first dilution of antibody concentration. These compounds were designated as weak binders. Nine compounds showed some kind of signal at the first dilution of antibody concentration and were thus designated as medium to strong binders. Of these, three compounds AB_0000860, AB_0000910 and AB_0001250 showing a clear signal (2 in table 1) were further analysed at a second dilution of antibody concentration (conc 3 in table 1). Whereas compound AB_0000910 did not show any signal at this concentration, both AB_0000860 and AB_0001250 did and were thus confirmed as strong binders.

As regards the structure-activity relationships, the following observations arose from inspection of the structures of the compounds belonging to the three groups of non-binders, weak binders and medium to strong binders. Preferable for binding seems to be the combination of an aromatic part with and aliphatic part with appropriate elements on both parts. Positive for binding for the aromatic part is a meta- and/or para-substituted phenyl ring without heteroatoms in the ring. Especially the presence of nitrogen in the ring seems to influence binding negatively as well as substituents in ortho position. Preferable for binding for the aliphatic part are 1) the presence of a tertiary anilinic nitrogen attached to position 1 and 2) (only) one β-keto group attached to position 1, position 1 being the position where the aliphatic part of the ligands is connected to the assumed deepest laying aromatic ring. Preferably a combination of both features like in the N,N-alkylated urea moiety found in the two hits confirmed as strong binders. AB_0000860 posses two aromatic rings differing by their relation to the keto groups of the hydantion ring. This asymmetry gives the molecule a direction, which from the docking analysis agrees with the requirement of only one keto group in a β-position relative to position 1.

The presence of two keto groups in a β-position relative to position 1 disfavours binding. This is in agreement with docking results, where it can be seen that a second keto group would probably be forced into a rather unfavourable hydrophobic environment. Also, larger ring-systems than six member rings (for instance fused rings) seem to have a negative influence for binding. Among the weak binders five compounds were found containing non-substituted phenyl rings and three compounds containing tri-fluoro-methyl groups. It could be speculated that for these compounds the affinity detected may be related to hydrophobic interactions of a rather non-specific type.

EXAMPLE 2

Directed Library

Actions Undertaken after the Analysis of the NMR Screening

From the analysis of the results, two directed libraries centred on the structures of the confirmed strongest binder AB_0001250 were created.

Directed Library Centred on the Structure of AB_0001250

Hit AB_0001250 was one of the hits designated as strong binders. Also, the structure as such offered a potentially attractive synthetic route for varying the substitution pattern of central motif, i.e. the tetra substituted urea, including the introduction of a handle for immobilisation, e.g. to a gel. Therefore, AB_0001250 was chosen as a starting point in the continued development of improvements.

The analysis started with a search for varying the substitution pattern of the aromatic ring. The di-chloro substituted aromatic ring that is present in AB_0001250 does according to the docking fill the available space in an appropriate way in two dimensions but, since that structure is planar, a pocket above the plane of the ring was not filled.

3-chloro-4-methoxyaniline was chosen as the starting point for further synthetic work, since it can be converted into the desired starting material by alkylation of the anilinic nitrogen with methyl iodide.

One option is to have a fluoro-substituent in the meta position, in order to favour hydrogen bonding of protein residues. Also for this, a suitable starting material, namely 3-chloro-4-methoxyaniline, is commercially available. The compounds belonging to the designed directed library together with the structure of the original hit AB_0001250 as shown in FIG. 3 were subject to docking and NMR screening.

EXAMPLE 3

Molecular Modelling and Docking of Directed Library

The modelling and docking was performed as described above under Materials and Methods. The results from the docking are as follows:

All docked compounds in the directed library with the exception of AB_0001256 resulted in a docked conformation inside the binding pocket, which very closely resembles the position of the docked hit AB_0001250, see FIG. 4. In four of the compounds, this is the best-ranked solution. In one of them (AB_0001252), the solution corresponding to the molecule inside the pocket is the second ranked solution. AB_0001256 lacks one of the methyl groups in the tetra substituted urea moiety. Consequently the corresponding amide bond should be more constrained to a planar geometry as compared to the remaining compounds in the library for which such geometry is forbidden because of steric effects between the methyl groups. Apparently, the non-planar geometry is of importance for docking.

The values of the obtained expected energies of binding in kJ/mol are −10, −13, −12, −14 and −14 for AB_000125 (−1) to (−5) respectively. Orthographic plots of the docked hits are shown in FIG. 5.

EXAMPLE 4

NMR Screening of Directed Library

TABLE 2

Results from NMR screening of the directed library

| ID | Trivial name | Conc 1 | Conc 2 |
|---|---|---|---|
| AB_0001251 | 4-(1,3-Dimethyl-3-phenyl-ureido)-butyric acid methyl ester | 0 | 0 |
| AB_0001252 | 4-[3-(3-Fluoro-4-methoxy-phenyl)-1,3-dimethyl-ureido]-butyric acid methyl ester | 1 | 1 |
| AB_0001253 | 4-[3-(3-Chloro-4-methoxy-phenyl)-1,3-dimethyl-ureido]-butyric acid methyl ester | 2 | 1 |
| AB_0001255 | 4-[3-(3,4-Dichloro-phenyl)-1,3-dimethyl-ureido]-butyric acid methyl ester | 2 | 2 |
| AB_0001257 | 4-[3-(3,4-Dichloro-phenyl)-3-methyl-ureido]-butyric acid methyl ester | 2 | 0 |
| AB_0001258 | 4-[3-(3,4-Difluoro-phenyl)-1,3-dimethyl-ureido]-butyric acid methyl ester | 1 | 1 |
| AB_0003090 | 4-[3-(3,4-Dichloro-phenyl)-1,3-dimethyl-ureido]-butyric acid |  |  |
| AB_0003290 | 1-[(3,4-Dichloro-phenyl)-methyl-carbamoyl]-pyrrolidine-2-carboxylic acid methyl ester (R-isomer) | 2 | 2 |

Concentration code as follows: conc. 1 means 500 and conc 2 100 nM antibody.
NMR signal code: 0 no, 1 weak and 2 strong signal, nd means not determined.

The compounds AB_0001251 through AB_0001259 and AB_0003130 through AB_0003150, shown Table 2, where screened at the two higher antibody concentrations. The result showed that all compounds except AB_0001251 were interacting with the antibody. It was also shown that compound AB_0001255, which is the original compound AB_0001250 with an extension, has the strongest binding of these compounds in the assay. Further, the results also showed that substituents on the aromatic ring are indispensable for binding in this type of compounds since the only negative result was obtained with the unsubstituted variants AB_0001251 and AB_0003150.

EXAMPLE 5

General Method for Attaching Ligand to Support

Sepharose™ HP (Amersham Biosciences, Uppsala, Sweden) that had previously been derivatised with allyl glycidyl ether was activated with bromine and coupled with hexamethylene-diamine according to a standard protocol. The free amine content was determined to 17 μmol/mL gel according to a standard protocol.

2 mL of this gel was transferred to a reaction vessel together with 2 mL of DMF. 1-(3-Dimethylaminopropyl)-3-ethylcarbodiimide hydrochloride (0.15 mmol) and diisopropyl amine (0.1 mmol) was added and the suspension was put on a shaker at 30° C. After 5 min. the ligand to be coupled (0.1 mmol) was added and the reaction was allowed to continue for 15 hours.

Thereafter the gel was transferred to a glass filter funnel and washed with a 1:1 mixture of DMF and acetic acid anhydride. The gel was allowed to be in contact with this solution for 30 min. whereafter it was washed with consecutively DMF, water, and 20% ethanol.

The amount of ligand coupled to the gel was determined with a NMR-method using tri-methoxy benzene as internal reference.

EXAMPLE 6

Chromatographic Characterisation of Affinity Media Containing the Ligand AB 0003291 According to the Invention AB__0003291 coupled to Sepharose™ HP (ligand concentration 11 μmol/ml gel as determined by MAS-NMR) was packed in 0.5 ml Tricorn™ 5/20 columns (Amersham Biosciences, Uppsala, Sweden) at a flow rate of 1-2 ml/min. Monoclonals ABFab-K1 (FAB/kappa), ABFab-K2 (Fab'2/kappa) and ABFab-L2 (Fab/lambda) were tested for binding to AB__0003291-containing gel using protein concentrations of 0.4 or 0.2 mg/ml in PBS, 1 M $(NH_4)_2SO_4$, pH 7. 100 μg of ABFab-K1 and 50 μg of the other two proteins were injected at a flow rate of 0.25 ml/min (contact time 2 min) using an Äkta™ Explorer 10 chromatography system equipped with a UV cell, pH meter, conductivity cell and auto-injector (Amersham Biosciences, Uppsala, Sweden). Protein loading was followed by a wash period of 20 column volumes of loading buffer (PBS, 1 M $(NH_4)_2SO_4$, pH 7) and a second wash step with 0.01 M of NaOH.

FIGS. 7, 8 and 9 show the separate injections of the monoclonals ABFab-K1, ABFab-K2 and ABFab-L2, respectively, on the AB__0003291-containing media. Evidently, the affinity column containing AB__0003290 coupled to Sepharose™ HP is able to bind the monoclonals ABFab-K1 and ABFab-K2, whereas monoclonal ABFab-L2 directly comes off the affinity column and is found in the flow-through. Elution of monoclonals ABFab-K1 and ABFab-K2 bound to the affinity column in PBS, 1 M $(NH_4)_2SO_4$, pH 7 is possible using different elution conditions such as 50 mM acetate buffer containing 0.14 M NaCl, pH 4 or PBS, pH 7 containing 10% n-propanol (data not shown).

What is claimed is:

1. A separation matrix for affinity chromatography, comprising ligands coupled to a support, wherein the majority of the ligands are the compounds of formula (I)

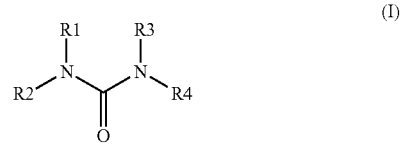

wherein
$R_1$ is $CH_3$ or $CH_2CH_3$;
$R_2$ is a phenyl group that has been substituted with Cl in meta and para position;
$R_3$ is H, $CH_3$ or $CH_2CH_3$; and
$R_4$ is a linear or cyclic aliphatic group,
or, wherein
$R_1$ and $R_2$ are as stated above while $R_3$ and $R_4$ are parts of a 4- to 6-membered cyclic entity,
and which compound has affinity for human IgG of κ-type;
further wherein said ligands are coupled to said support through the group $R_4$.

2. The separation matrix of claim 1, wherein the ligands have been coupled to the support via linkers.

3. The separation matrix of claim 1, wherein the support is a porous polymeric particle.

4. A system suitable for affinity chromatography, comprising the separation matrix of claim 1 packed in a column.

5. The separation matrix of claim 1, wherein the compounds of formula (I) is an affinity ligand with affinity for the constant region of a Fab fragment of human IgG of κ-type.

6. The separation matrix of claim 1, wherein $R_1$ is $CH_3$.

7. The separation matrix of claim 1, wherein $R_1$ is $CH_3$; and $R_3$ and $R_4$ are parts of a cyclic 5-membered group.

8. The separation matrix of claim 7, wherein the cyclic 5-membered entity is substituted in a position directly adjacent to N with a C(O)—O—CH3 group.

9. The separation matrix of claim 1, wherein said compounds of formula (I) are capable of binding to the constant region of a human IgG of κ-type, or a functional derivative thereof, with a binding constant of at least $10^{-3}$ M.

10. The separation matrix of claim 1, wherein said compounds of formula (I) are capable of binding to the constant region of a human IgG of κ-type, or a functional derivative thereof, via a binding pocket-defined by the structure coordinates of the amino acids as shown in FIG. 6.

* * * * *

UNITED STATES PATENT AND TRADEMARK OFFICE
CERTIFICATE OF CORRECTION

PATENT NO. : 7,645,903 B2
APPLICATION NO. : 10/531783
DATED : January 12, 2010
INVENTOR(S) : Axén et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 866 days.

Signed and Sealed this

Sixteenth Day of November, 2010

David J. Kappos
*Director of the United States Patent and Trademark Office*